United States Patent [19]
Asgari et al.

[11] Patent Number: 5,861,253
[45] Date of Patent: Jan. 19, 1999

[54] INTRACELLULAR ANTIGENS FOR IDENTIFYING FETAL CELLS IN MATERNAL BLOOD

[75] Inventors: Morteza Asgari; Mark Blick, both of Houston; Joel Bresser, Bellaire; Michael Lee Cubbage; Nagindra Prashad, both of Houston, all of Tex.

[73] Assignee: Aprogenex, Inc., Houston, Tex.

[21] Appl. No.: 775,607

[22] Filed: Dec. 31, 1996

Related U.S. Application Data

[63] Continuation of Ser. No. 374,144, Jan. 17, 1995, Pat. No. 5,629,147, which is a continuation of PCT/US94/08342, filed Jul. 19, 1994, and a continuation-in-part of PCT/US93/06828, filed Jul. 19, 1993, which is a continuation of Ser. No. 94,710, Jul. 19, 1993, abandoned, said Ser. No. 374,144, is a continuation-in-part of Ser. No. 94,710, which is a continuation-in-part of Ser. No. 915,965, Jul. 17, 1992, abandoned.

[51] Int. Cl.$^6$ .............................. C12Q 1/68; G01N 33/53; C07H 21/04; C07K 14/435
[52] U.S. Cl. ................................... 435/6; 435/5; 435/7.1; 435/40.5; 435/40.51; 435/7.21; 435/7.24; 435/7.25; 536/24.31; 536/24.32; 530/388.2; 530/388.22; 530/388.7; 530/389.6; 935/9; 935/77; 935/78
[58] Field of Search ........................... 435/5, 6, 7.1, 40.5, 435/40.51, 7.21, 7.24, 7.25; 536/24.31, 24.32; 530/388.2, 388.22, 388.7, 389.6; 935/78, 8, 9

[56] References Cited

U.S. PATENT DOCUMENTS 5,731,156   3/1998   Golbus ...................................... 435/7.1

FOREIGN PATENT DOCUMENTS 0357436   3/1990   European Pat. Off. .
9107660   5/1991   WIPO .

OTHER PUBLICATIONS

Kulozik et al (1982) Human Genetics 62: 221–224.

*Primary Examiner*—Carla J. Myers
*Attorney, Agent, or Firm*—Elman & Associates

[57] ABSTRACT

Fetal cells may be obtained from amniocentesis, chorionic villus sampling, percutaneous umbilical cord sampling or in vitro fertilization embryos or products of conception, but are preferably from maternal peripheral blood. Fetal cells may be enriched by density gradient centrifugation. Fetal cells may also be enriched by removing maternal cells with an antibody to a cell surface antigen, e.g. anti-CD45, either immobilized or by fluorescence-activated cell sorting. Fetal cells are also distinguishable from maternal cells by staining, e.g. with a labeled antibody to cytokeratin or to fetal hemoglobin, or for fetal hemoglobin by hematoxylin/eosin, or by in situ hybridization to detect one or more fetal mRNAs, e.g., of fetal hemoglobin or fetoprotein. Amplification may be used in conjunction with the in situ hybridization. Fetal cells circulating in maternal blood may be separated by flow cytometry, sorting on their intrinsic light scattering properties. Fetal nucleated erythrocytes may be identified by a label for fetal hemoglobin. Fetal cells may be treated to determine genetic characteristics or abnormalities, infectious agents or other properties by nucleic acid hybridization. Genetic abnormalities may include deletions, additions, amplifications, translocations or rearrangements. Multiple abnormalities may also be detected simultaneously, and they may be visually distinguished by color. Kits are provided for the disclosed procedures.

13 Claims, 17 Drawing Sheets

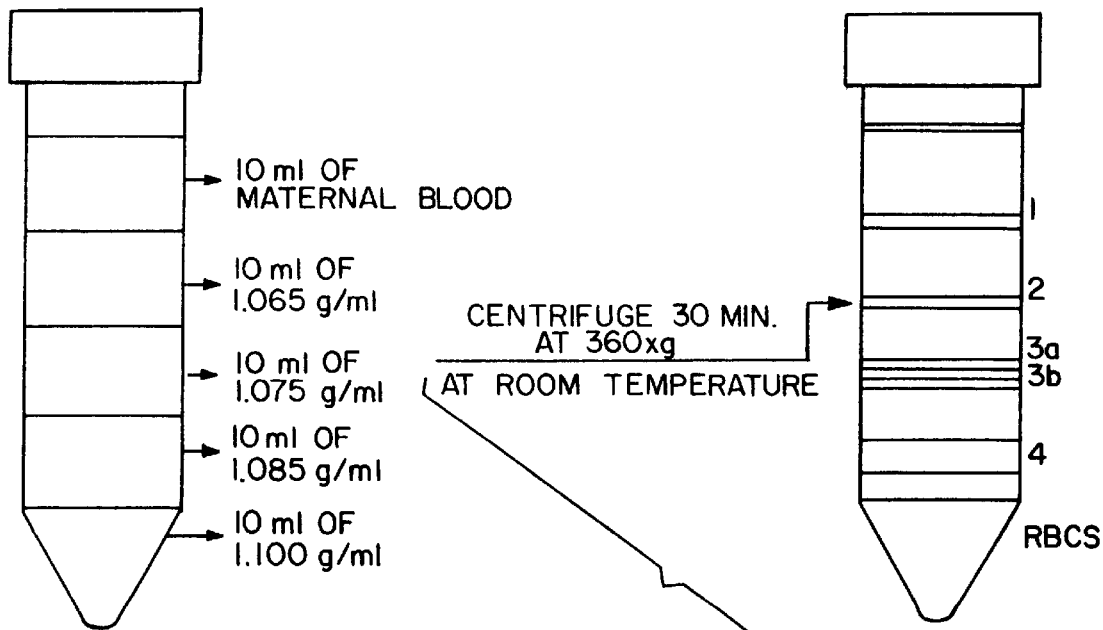
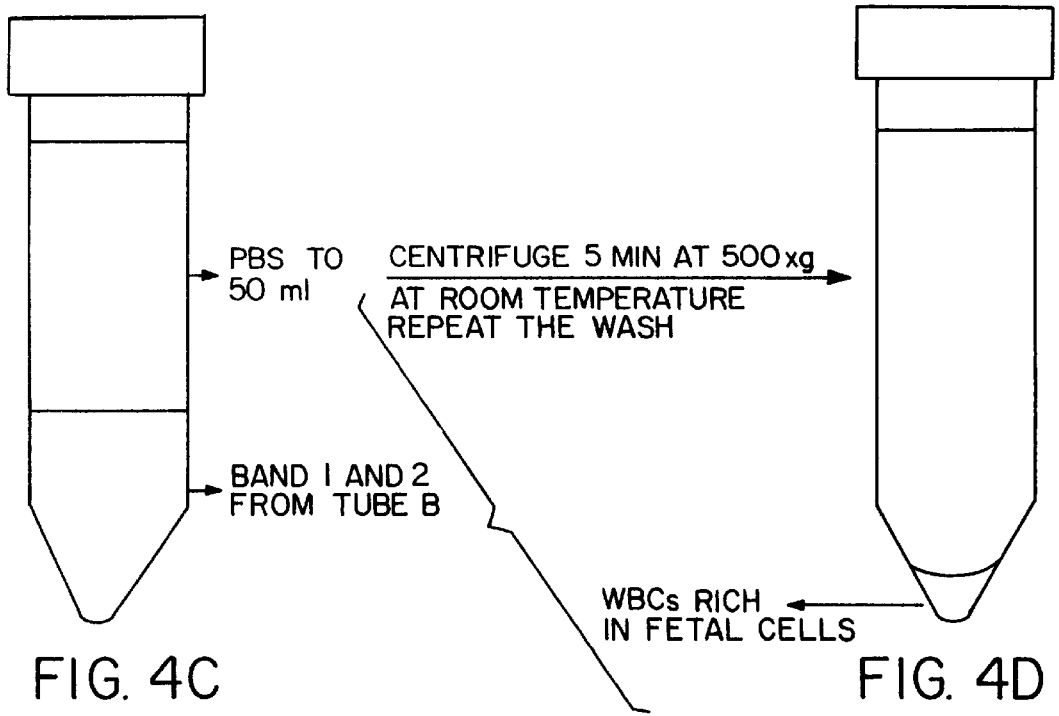
FIG. 4A  FIG. 4B  FIG. 4C  FIG. 4D

INTRACELLULAR ANTIGENS FOR IDENTIFYING FETAL CELLS IN MATERNAL BLOOD

CROSS REFERENCE TO RELATED APPLICATIONS

This is a continuation of U.S. application Ser. No. 08/374,144, filed Jan. 17, 1995, now U.S. Pat. No. 5,629,147, which is: a continuation of U.S. application Ser. No. 08/094,710, filed Jul. 17, 1993, abandoned; and a continuation of International patent application PCT/US94/08342, filed Jul. 19, 1994, which in turn is a continuation-in-part of U.S. application Ser. No. 08/094,710, filed Jul. 17, 1993, abandoned; and a continuation-in-part of International patent application PCT/US93/06828, filed Jul. 19, 1993, which in turn is a continuation-in-part of U.S. application Ser. No. 07/915,965, filed Jul. 17, 1992, abandoned.

FIELD OF THE INVENTION

This invention generally pertains to a method of enriching fetal cells from maternal blood and to a method for identifying such fetal cells, and further to a process whereby such cells are specimens in an in situ hybridization to detect nucleic acid sequences of clinical interest, e.g. to identify the sex of a fetus, and to detect genetic abnormalities and/or viral infections in fetal cells.

BACKGROUND OF THE INVENTION

The sex of a human fetus and certain fetal chromosomal abnormalities are conventionally detected or confirmed by directly examining the chromosomes in fetal cells by cytogenetic analysis or by testing for specific sequences of DNA within the chromosomes using nucleic acid analysis. These tests require the collection and culturing of living cells obtained through an outpatient surgical procedure involving some risk to the mother or fetus. Cells, which have been shed from the fetus, may be obtained by amniocentesis. Amniocentesis involves inserting a needle through the abdominal wall into the uterus and withdrawing a small amount of amniotic fluid. An alternative procedure involves sampling the tissue of chorionic villi from the surface of the placenta by inserting a catheter through the cervix or abdomen. However, spontaneous miscarriage or other serious complications may occur in about 0.5% of amniocentesis procedures and about 1% of chorionic villus procedures. Fetal cells collected by amniocentesis or chorionic villus sampling are grown in culture for several days and then examined for abnormalities.

Various kinds of fetal cells have been characterized. Fetal cells include, but are not limited to, fetal erythrocytes, lymphocytes or trophoblasts. Trophoblasts include cytotrophoblast or syncytiotrophoblast cells and cells which may be sampled from embryos produced by in vitro fertilization techniques. As used herein, the term "erythrocytes" includes erythroblasts, normoblasts and reticulocytes, as well as erythrocytes, unless the contrary is clear from the context.

It is known that a small number of fetal cells circulate in the mother's blood. About one in 4,000 to 7,000 fetal erythrocytes in the maternal blood circulation is a fetal nucleated red blood cell. Methods for detecting certain of the fetal cells and/or separating them from the mother's blood have been reported. See, e.g., S. C. Yeoh et al., Prenatal Diagnosis 11:117–123 (1991); U. W. Mueller et al., Lancet 336:197–200 (1990) (isolation of fetal trophoblasts by murine monoclonal antibodies); J. O. Price et al., Am. J. Obstet. Gynecol. 165:1731–37 (1991) (fetal nucleated erythrocytes were flow sorted on the basis of four parameters: cell size, cell granularity, transferrin receptor, and glycophorin-A cell surface molecule); PCT Publication No. WO 91/07660 to Childrens Medical Center Corp. (a method for isolating fetal nucleated erythrocytes by means of an antigen present on the cell surface of the fetal erythrocytes); PCT Publication No. WO 91/16452 of Cellpro Incorporated; and United States Patent No. 5,153,117 (a method for selectively recovering fetal cells from a maternal blood sample where cells of the sample are combined with a first and second antibody labeled with different fluorochromes).

Nucleic acid hybridization techniques are based on the ability of single-stranded DNA or RNA to pair, i.e. hybridize, with a complementary nucleic acid strand. This hybridization reaction allows the development of specific probes, or populations of probes, that can identify the presence of specific genes (DNA) or polynucleotide sequences of the transcription of those genes (RNA).

By the use of specific nucleic acid (RNA or DNA) probes, genetic markers for the gender or other genetic characteristic of the fetus and for infection and other disease states may be detected. Certain genetic diseases are characterized by the presence of genes absent in normal tissue. Other disease conditions are characterized by the expression of RNAs or RNA translation products (i.e. peptides or proteins) which are not expressed in normal cells. Some disease states are characterized by the absence of certain genes or portions of genes, or the absence or alteration of expression of gene products or proteins. Moreover, it is often desired to characterize the gender of animal fetuses, such as bovine fetuses, as well as human.

For background on nucleic acid genetic testing, see e.g., P. G. McDonough, Sem. Perinatol. 9:250–256 (1985), and W. G. Butler, et al, Fertility & Sterility 51:375–386.

Solution hybridization methods require the destruction of the cell and the isolation of the nucleic acids from the cell before carrying out the hybridization reaction. These methods sacrifice cellular integrity, spatial resolution and sensitivity of detection. Where relatively few cells are available for isolation, as with fetal cells circulating in maternal blood, solution hybridization is not feasible.

Amplification of nucleic acids, such as by the polymerase chain reaction, is a known technique, but with certain known drawbacks preventing optimal speed and efficiency. For example, such techniques may cause lysis of cells, may produce false positives due to sensitivity of the technique, and may lead to loss of specificity where high levels of amplification are required to detect a target that is present in low copy number. Moreover, hybridization of the amplified target is required in any event, so that multiple time-consuming steps are performed when amplification is used.

In situ hybridization provides a technique for the determination and quantitation of nucleic acids (DNA and RNA) in tissues at the single-cell level. Such hybridization techniques can detect the presence or absence of specific genes in cells and may also be utilized to detect the expression of gene products at the single-cell level.

In situ hybridization procedures are disclosed in U.S. Pat. No. 5,225,326 and copending U.S. patent application Ser. No. 07/668,751. The disclosure of each patent, patent application and journal publication identified in this patent application is incorporated by reference.

Despite the aforementioned knowledge, the prior art remains deficient. A truly rapid, sensitive, efficient and practical method of determining fetal gender and of detecting fetal genetic abnormalities on a routine basis without invading the mother's womb is lacking. Thus, the present invention fulfills a long-felt need and desire in this field.

SUMMARY OF THE INVENTION

In one set of embodiments of the present invention, there is provided a method of identifying a fetal erythrocyte in a specimen. In these embodiments, cells may be obtained from maternal peripheral blood, umbilical cord blood, chorionic villus samples, etc. Cellular samples may be used directly or may be concentrated as stated elsewhere herein to enrich the population of fetal cells prior to analysis. Cells may be fixed in common precipitating fixatives or cross-linking fixatives or may be used in the following test without fixation. The procedure may be carried out with cells deposited on a solid support such as a glass microscope slide or used with the cells in suspension.

This method comprises the steps of obtaining a specimen that contains fetal cells and detecting a marker that distinguishes fetal cells from maternal cells also present in the sample.

The most preferred method of identifying a cell as a fetal erythrocyte in accordance with the present invention is to detect the presence of RNA for fetal hemoglobin (HbF) or embryonic hemoglobin. Such RNA is generally messenger RNA (mRNA), but may alternatively or additionally include heteronuclear RNA (hnRNA). Also, unless the context requires a contrary interpretation, the term messenger RNA or mRNA herein includes ribosomal RNA (rRNA). The presence of such RNA indicates that the gene for the fetal protein is being transcribed and expressed. Such detection is preferably performed within cells with substantially intact cellular membranes using in situ hybridization, preferably with synthetic DNA probes complementary to the fetal protein RNA.

In a preferred embodiment synthetic DNA probes are employed, to which chromofluors have been covalently attached. The binding of such probes to fetal-cell-specific RNA within cells may be observed under the microscope as a bright fluorescence or may be detected by fluorimetric apparatus. By "fluorescence" we refer to any emission of detectable radiation as a result of excitement with radiation of a different wavelength than that emitted. The exciting radiation is conventionally ultraviolet or visible light but may be infrared or other electromagnetic radiation.

Another preferred embodiment employs synthetic DNA probes which are directly labeled, or may be indirectly labeled with enzymes such as alkaline phosphatase. The binding of such probes to fetal RNA followed by subsequent reaction of the enzymes with substrates to produce a detectable product (e.g. blue or purple solid precipitated from the reaction of BCIP with NBT) may be observed under the microscope.

The information resulting from such an assay may be used not only to identify the status of the fetus, as will be discussed more particularly below, but also to provide a fetal hemoglobin estimation based on the number of fetal erythrocytes detected, e.g. so as to assess the amount of fetal-maternal hemorrhage in case of Rh incompatibility. The amount of specific gamma globulin, containing anti Rh(D) to be administered, is calculated from this estimation, to suppress maternal immune reaction to fetal red blood cells entering maternal circulation.

Another method for identifying fetal erythrocytes is to detect a substance that is present in fetal cells but not in the maternal blood cells which would be present in the sample. One such substance which is particularly effective for such detection is fetal hemoglobin, which may be detected by a stain such as acid hematoxylin and eosin B (e.g. Sigma Diagnostics, P.O. 14508, St. Louis, Mo. 63178, cat. no. 285) or by an antibody to fetal hemoglobin. Another such substance is the Y chromosome present in male fetal cells but absent from the cells of the mother that may be detected by in situ hybridization.

Yet another method for identifying fetal cells is to detect an RNA and a peptide that are present in fetal cells. The RNA may be detected by nucleic acid hybridization, and the peptide may be detected as aforesaid, by the binding of an antibody thereto or by staining.

In another embodiment of the invention, a fetal-cell-specific RNA sequence is detected by hybridization as aforesaid, along with another marker for the cells of interest, such as staining of fetal hemoglobin by hematoxylin and eosin or such as binding of a labeled monoclonal antibody with an antigen present in the cells of interest.

Another embodiment of the present invention detects the presence of at least two different RNAs in a cell. Fetal cells contain unique mRNAs or mRNA species which are produced in cell types which do not normally contain the particular mRNA species. The detection of these RNAs, whether detected as mRNAs or hnRNAs can serve to identify cells, or even subcellular fractions, as fetal or embryonic in origin.

Certain RNA populations are present in high abundance (e.g., fetal hemoglobin in fetal nucleated red blood cells), other fetal- or embryonic-specific RNAs are present in low abundance, either alone or even when measured in a population of fetal-specific RNAs. In addition, certain RNA species, while produced in certain fetal cells, may also be produced in certain maternal cells. However, there are situations where fetal cells express two or more particular RNAs in the same cell while maternal cells from the same specimen source do not contain both RNA species in the same cell. The ability to detect multiple mRNA or hnRNA species simultaneously in the same cell thereby enhances the ability to distinguish fetal cells from non-fetal (e.g. maternal) cells and offers a means of combining the signal produced when only the unique set of RNAs is present so that a specific signal is detected, which uniquely identifies fetal erythrocytes. In one embodiment of the invention, two or more RNA sequences are detected, using one or more probes for a first RNA sequence and one or more probes for a second RNA sequence. The probes for the first sequence are labeled to provide a first signal, such as a greenish fluorescence, and the probes for the second sequence are labeled to provide a signal that is different from the first signal, such as a reddish fluorescence. When the combination of both signals are detected in a single cell, which in this illustration would appear as an orange fluorescence, then both RNAs are found and thus a fetal cell has been detected.

In a particular embodiment of the aforesaid process, DNA probes are prepared for fetal hemoglobin RNA, labeled with a first fluorescer, such as fluorescein. DNA probes are also prepared for RNA of embryonic hemoglobin, $\epsilon$ chain, labeled with a second fluorescer, such as Cy5. DNA probes are also prepared for RNA of embryonic hemoglobin, $\zeta$ chain, labeled with a third fluorescer such as Cy3. When all three of these RNAs are detected in a single cell, the cell observed under a fluorescent microscope lights up with an intense orange fluorescence, being the addition of the yellow-green of fluorescein, yellow-orange of Cy3, and reddish of Cy5. Such a procedure also may be automated.

A further set of embodiments of the present invention involve enriching the relative proportion of fetal cells in the specimen compared to other cells, e.g. maternal cells by selective removal of maternal cells. Such enrichment may preferably take place by selectively removing maternal cells, e.g. by contacting the sample with a ligand to a cell surface component, the ligand being capable of being selectively separated from the sample. Preferably the ligand is an antibody to an antigen generally present on maternal blood cells. Desirably the ligand is bound to a solid matrix for separation from the liquid containing the sample. Preferably the matrix is a magnetic bead. The matrix may alternatively be in the form of a column through which the cell suspension is passed. Liquid electrophoresis in which cells are subjected to an electric field and separated on the basis of their intrinsic charge may be used. Passage through a filtration system that separates cells on the basis of their intrinsic charge may also be used.

In a preferred embodiment, the antibody comprises a monoclonal antibody to cluster-determinant-45 (hereinafter "CD" refers to cluster determinant as in, "CD45"). This antibody selectively binds to an epitope expressed on all isoforms of the human leukocyte common antigen family, which are expressed on all leukocytes. Fetal erythrocytes are preferably enriched in such manner. Additional antibodies which may be employed, along with or instead of anti-CD45, include anti-CD13, anti-CD34, anti-CD44 and anti-CD31. Preferably the amount of antibody used is from about 2 to about 20 µg per million leukocytes in the sample.

Alternatively, or in addition to the aforesaid, fetal erythrocytes may be selectively enriched by density gradient centrifugation. Subsequently, the fetal cells are detected as generally stated hereinabove.

In another embodiment of the present invention, there is provided a novel method of identifying fetal cells in a specimen. This method comprises the steps of obtaining a specimen that contains fetal cells and examining the cells by flow cytometry without any preliminary labeling of the fetal cells through the use of a fluorescent label or any other label that may generate a fluorescent signal. Fetal cells are identified solely on the basis of their intrinsic light scattering properties. Simultaneously the fetal cells are concentrated using flow cytometry. This method relies on the unique finding that fetal call have distinguishable intrinsic light scattering properties that allow them to be sorted from many other cells. Fetal nucleated erythrocytes scatter light in a manner similar to that of monocytic cells and are thus usefully enriched by sorting them away from numerous other cells types.

In yet another embodiment of the present invention, there is provided a novel method of identifying fetal cells in a specimen. This method comprises the steps of obtaining a specimen that contains fetal cells and preliminarily labeling the fetal cells through the use of a fluorescent label or a label which may generate a fluorescent signal by enzymatic action or a label which may react antigenically to generate a fluorescent signal, which signal may be detected by instrumentation. Subsequently, the fetal cells are concentrated using flow cytometry.

In yet another embodiment of the present invention, there is provided a kit for the enrichment of fetal erythrocytes within a blood specimen including means for creating a density gradient for enriching fetal cells of interest.

In still yet another embodiment of the present invention, there is provided a novel kit for the enrichment of fetal erythrocytes from a specimen, such as preferably maternal peripheral blood, and the detection of nucleic acid sequence in such fetal cells. This kit comprises an antibody to a cell surface antigen present on most or all adult white blood cells, which antibody may be bound to a matrix to facilitate separation. The kit further comprises a hybridization solution comprising a denaturing agent, hybrid stabilizing agent, buffering agent, and a membrane pore-forming agent. In addition, this kit contains a supply of an oligonucleotide probe capable of hybridizing with a target fetal RNA nucleotide sequence. Advantageously, such a kit also includes another detectably different probe capable of hybridizing with a nucleic acid sequence of clinical interest. Such kits typically include instructions for their use.

Various kinds of fetal cells are characterized by cell type. In a preferred embodiment, this invention relates to fetal nucleated erythrocytes. The fetal cells are preferably separated from maternal peripheral blood by ligand binding of maternal cells or density gradient centrifugation. However, the procedures of the present invention may alternatively be applied to samples obtained by percutaneous sampling of umbilical cord blood, amniocentesis, chorionic villi sampling or other procedures, if the advantages obtained by maternal peripheral blood sampling are not required.

Alternatively, certain methods of the present invention may involve embryonic cells fertilized in vitro, or products of conception, which do not need to be separated or distinguished from maternal cells.

Following enrichment of the fetal erythrocytes as mentioned above, fetal cells may be distinguished or separated from maternal cells by recognition of a fetal cell antigen. Various antibodies have been used to discriminate between fetal and maternal cells. An antibody to cytokeratin attached to a fluorescent label is especially desirable for use without interfering with the nucleic acid hybridization performed in accordance with the present invention. E.g., cells may be distinguished by staining with a labeled antibody to fetal hemoglobin, by staining for fetal hemoglobin, or preferably by in situ hybridization using DNA probes to messenger RNA (mRNA) sequences that are present in such fetal cells but not in maternal blood cells.

However, a preferred method in accordance with this invention, uses in situ hybridization performed on cells that are obtained from maternal peripheral blood using probes and conditions that select for messenger RNA (mRNA) bearing sequences that are transcribed in fetal cells but not in the maternal blood cells. In accordance with the present invention, it has been found that mRNA for fetal hemoglobin (HbF) is an especially good marker of such cells for detection by in situ hybridization.

An advantage of the hybridization technique of a preferred embodiment of the present invention is that it is possible to perform the hybridization to detect fetal mRNA sequences under conditions similar to (or preferably the same as) those used to detect genetic or viral DNA. Moreover, in a most preferred embodiment, a single incubation step is performed in which probes for mRNA and probes for DNA are present in the hybridization cocktail.

The present invention employs in situ hybridization techniques that are capable of detecting even a single genetic abnormality in a single cell. Incubation in accordance with the present invention is desirably less than about 120 minutes, and preferably between about 5 and about 30 minutes.

Fetal cells contain unique mRNAs or mRNA species which are produced in cell types which do not normally contain the particular mRNA species. The detection of these RNAs, whether detected as mRNAs or hnRNAs, can serve to identify cells, or even subcellular fractions, as fetal or embryonic in origin. While certain RNA populations, such as fetal-hemoglobin mRNA in fetal nucleated erythrocytes, are present in relatively high abundance, other fetal- or embryo-specific mRNAs are present in low abundance, either alone or even when considered as part of a population of fetal-specific mRNAs. In addition, certain RNA species, although produced in certain fetal cells, may also be produced in certain maternal cells. However, there are situations where fetal cells express two or more particular mRNAs in the same cell whereas maternal cells from the same specimen do not contain both mRNA species in the same cell. The ability to detect multiple mRNAs or hnRNA species simultaneously in the same cell thereby enhances the ability to distinguish fetal cells from non-fetal (e.g. maternal) cells and offers a means of combining the signals produced when only the unique set of RNAs is present, so that a more specific signal, which uniquely identifies fetal cells, is detected.

One may also wish to determine the tissue of origin of unknown cellular samples, such as may occur in crime scene investigations. Moreover, in clinical analyses of potential or actual oncologies, knowledge of the tissue of origin, e.g. prostate or breast, of a metastatic cell may assist in the detection or treatment of cancers. The present technique may be employed for such purposes by seeking to detect the particular population of RNAs known to distinguish one such tissue from another.

BRIEF DESCRIPTION OF DRAWINGS

FIGS. 1B-1 and 1B-2 show the use of in situ hybridization to determine the numerical status of chromosomes X in normal female amniocytes.

FIGS. 1C-1 and 1C-2 show the use of in situ hybridization to determine the numerical status of chromosomes 18 in normal amniocytes.

FIGS. 2A-1 and 2A-2 show the simultaneous detection of the X and Y chromosomes within amniocytes and white blood cells.

FIGS. 2B-1 and 2B-2 show the simultaneous detection of the X and Y chromosomes within amniocytes.

FIG. 4A shows a schematic representation of the layering technique preferably used to enrich fetal trophoblasts from maternal blood in accordance with the present invention prior to centrifugation.

FIG. 4B shows a schematic representation of the layering technique preferably used to enrich fetal trophoblasts from maternal blood in accordance with the present invention after centrifugation.

FIG. 4C shows a schematic representation of the recovery of cells from the tube schematically depicted in FIG. 3B and the dilution with PBS prior to centrifugation.

FIG. 4D shows a schematic representation of the centrifuge tube schematically depicted in FIG. 3C after centrifugation.

FIGS. 9A-1 and 9A-2 show the use of in situ hybridization with cytokeratin probes to positively identify amniocytes and trophoblasts.

FIGS. 9B-1 and 9B-2 show the use of in situ hybridization with HCG probes to positively identify amniocytes and trophoblasts.

FIGS. 9C-1 and 9C-2 show the use of in situ hybridization with alpha-fetoprotein probes to positively identify amniocytes and trophoblasts.

DESCRIPTION OF THE PREFERRED EMBODIMENTS

Figures 1, 1A:
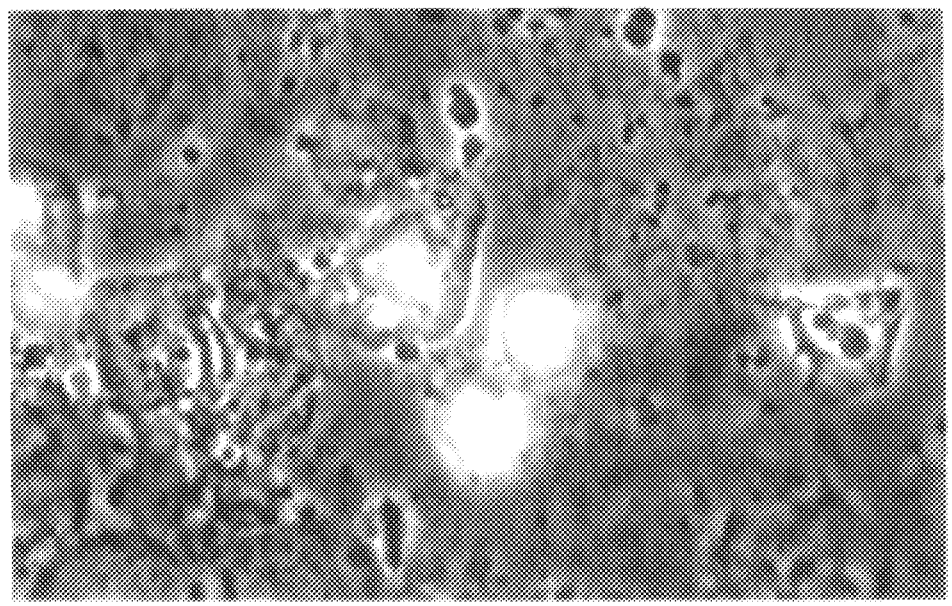
FIGS. 1A-1 and 1A-2 show the use of in situ hybridization to determine the numerical status of chromosomes Y in normal male amniocytes.
Figures 1, 1A, 2:

The methods of the present invention may be used to identify fetal cells in a wide variety of specimens. Representative examples of such specimens include maternal peripheral blood, placental tissue, chorionic villi, amniotic fluid and embryonic tissue. For the reasons stated above, maternal peripheral blood is the preferable specimen. However, in the past this has been the most difficult specimen with which to obtain reliable and consistent results with because of the high ratio between maternal cells (which interfere with any assay of fetal nucleic acid) and fetal cells. Preferably, the methods of the present invention are used to detect fetal nucleated red blood cells.

The methods of the present invention may be used to detect fetal-cell-specific polynucleotide sequences, that is, oligonucleotides, within a fetal cell. Without limiting the present invention, the novel methods of the present invention may be used to detect a virus or a chromosome within a fetal cell. Representative examples of viruses detectable by the present invention include a human immunodeficiency virus, hepatitis virus and herpes virus. Representative examples of chromosomes detected by the present invention include the human chromosome X, chromosome Y, and Chromosomes 1, 13, 16, 18 and 21.

The sensitivity of the in situ hybridization techniques described herein permit the visual and photographic detection of a single copy of a genetic sequence present within a single cell and the detection and isolation by flow cytometry of cells containing a single copy of a genetic sequence.

The present invention allows for multiple targets to be tested simultaneously, using a single sample of cells. This permits the maximum amount of information to be obtained from a single sample, minimizing the need for multiple fetal cell samples and thereby decreasing the danger to both mother and fetus and minimizing need for cell purity and sorting.

Differentiation of Maternal Cells from Fetal Cells

Identification of fetal cells or detection of genetic abnormalities within fetal cells requires their separation and differentiation from maternal cells. This requirement is especially necessary when the sample of cells is obtained from maternal peripheral blood containing a low percentage of fetal cells. We have found, in accordance with the present invention, that negative separation by antibodies is particularly advantageous. We employ an antibody or antibodies binding specifically to maternal cell antigens and not significantly to fetal cell antigens. The antibodies may be coupled to numerous solid surfaces or supports (substrates, such as containers, columns, wells, beads, or particles) by physical or chemical bonding. Alternatively, the antibodies may be coupled to a material which facilitates the selected separation step. For example, antibodies may be labeled with fluorescent markers and cells to which these labeled antibodies bind may thereby be separated with a cell sorter by standard procedures.

In general, such antibodies are effective when employed in amounts of about 2–20 μg per million cells to which they are targeted. That is, antibodies which recognize and bind to leukocytes are added in the aforesaid amount, based on the expected number of leukocytes in the sample. Alternatively, antibodies which recognize and bind to trophoblasts are added in the aforesaid amount, based on the expected number of trophoblasts.

A particularly preferred separation is performed by using an antibody to anti-CD45 which selectively binds to white blood cells. The anti-CD45 is desirably bonded to a solid support such as magnetic beads, which may be introduced into a test tube and shaken with the sample and then held in position at the side of the test tube by the application of a magnetic field, while liquid containing the un-bound sample is removed. Such beads are available as Anti-CD45 immunomagnetic beads, Catalog No. 1178, from Amac, Inc., 160B Larrabee Road, Westbrook, Me. A preliminary step involving lysis of maternal erythrocytes involving, e.g. with ammonium chloride, can conveniently be used to remove a substantial proportion of these red cells.

Alternatively, one may obtain immunomagnetic beads from Calbiochem, 10933 N. Torrey Pines Road, La Jolla, Calif., uncoated as catalog no. 400995, or coated with streptavidin as catalog no. 400996. Such beads may be coated by the user with antibodies to cell surface antigens found on cells which are desired to be removed from the fetal cells. Another bead which may be coated with antibody is an aqueous suspension of iron oxide particles coated to provide carboxyl groups, permitting the covalent attachment of biologically active molecules. Such beads, and a description of procedure for use, are available as BioMag Carboxyl Terminated, catalog no. 8-4125, Advanced Magnetics, Inc., 735 Concord Ave., Cambridge, Mass. 02138.

If desired, white blood cells may be removed by using specific ligand/ligand-target interactions. Cells may be effectively removed by a combination of antibodies to CD45, CD13 and CD34. Anti-CD44 can also be included in the mixture to remove contaminating maternal red blood cells. Addition of anti-CD31 can specifically remove the contaminating platelets. Such antibodies are available from various sources such as Amac, Inc. (see above), Becton Dickinson, Franklin Lakes, N.J. 07417-1884, and Zymed Laboratories, Inc., 458 Carlton Court, South San Francisco, Calif. See Zymed's 1992 catalog at pages 10–13 and 71–72. See also W. Knapp, *Fourth International Workshop and Conference on Human Leukocyte Differentiation Antigens*, Oxford University Press, 1989; and D. F. Keren, *Flow Cytometry in Clinical Diagnosis*, pp. 41–87 ASCP Press, Chicago, 1989. Other ligand/ligand-target interactions may usefully be used, e.g. transferrin may be used to bind cells bearing the transferrin receptor.

Fetal cells may alternatively be isolated from maternal peripheral blood by either density gradient centrifugation or by flow cytometry. Using flow cytometry, fetal cells may be identified and sorted, for example, by examination of their light scattering properties alone. Alternatively, the fetal origin of such cells may be confirmed by first using either a labeled antibody specific for a fetal cell antigen or by using a nucleic-acid-specific probe, e.g., a synthetic oligonucleotide probe hybridizable to fetal cell RNA. Additionally, hemoglobin A chain mRNA may be detected in maternal cells and its presence used as a distinguishing feature.

Specific nucleic acid (RNA or DNA) probes may also be used as markers for the expression of genetic characteristics of a fetus which may be qualitatively or quantitatively distinct from those of the parent or normal adults. Thus, the presence of Y chromosome encoded genes or gene products is a qualitative distinguishing feature of the cells of a male fetus. Markers inherited by the fetus from the paternal genome also may be used to qualitatively distinguish fetus cells from maternal cells. In syndromes characterized by genetic abnormalities, e.g. chromosomal trisomies, quantitative differences in genetic constitution may be detected. In other syndromes, characterized by decreases or increases in copy number of genetic repetitive elements, quantitative differences in genetic constitution may also be detected. Quantitative differences in RNA may also arise because of the expression of fetal forms of genes that are not expressed, or are only expressed at a low level, in normal adult cells and tissues.

Preparation of Samples

Samples of peripheral blood (20 ml) are drawn from donors into Vacutainer tubes containing EDTA. Samples are stored and transported at temperatures not exceeding 4° C. and are not stored for more than 36 hours. Samples whose temperature exceed 10° C. upon receipt are rejected. Samples are collected from pregnant women of 10–24 weeks gestational age. In experiments that involved mixing blood from different donors the blood group of the samples is determined and only samples which have the same blood group are mixed.

Density Gradient Separation of Nucleated Cells from mixed Adult and Cord Blood

Twenty microliters (20 μl) of cord blood is added to 20 ml of the adult blood. The sample is thoroughly mixed and diluted with 2 volumes of Cell Buffer A (CBA). The diluted sample is then layered on a density gradient material (e.g., Ficoll-Hypaque, Histopaque, Percoll, etc.) which has a density of 1.107 g/ml. Centrifugation and separation are carried out according to the manufacturer's instructions. The buffy-coat of cells at the interface is then collected and washed once with CBA.

Preparation of Slides

If slides are to be prepared, they are preferably made by the conventional cytospin technique. Alternatively they may be prepared as organosilanated slides.

For cytospun slides, 200 μl of the cell suspension is cytospun onto each slide for five minutes at 500 rpm. The cytospun slides are dipped in chilled 80% ethanol/water (v/v) for five minutes and air dried.

Alternatively, the cytospun slides may be fixed by directly applying 30 μl of ethanol/methanol (3:1 v/v) onto each slide.

To prepare organosilanated slides, clean slides are immersed for 2 minutes in a freshly prepared 2% (v/v) solution of an organosilane such as 3-aminopropyltriethoxysilane in acetone. The slides are rinsed twice in water and air dried. For each 20 ml of maternal blood or 10 ml of umbilical cord blood used as the sample, the cell pellet is resuspended in 50 μl of a fixative solution, e.g. 80% ethanol/water or 3:1 ethanol/methanol. Fifty μl of this suspension is spotted on a slide and air dried.

Flow Cytometry

Cells are analyzed and sorted on a flow sorter based on the properties of the cells to scatter light forward and to the side. In each experiment parameters are empirically established regarding the forward and side scatter properties. In general, the gain on the photomultiplier tubes detecting the forward-scattered light and the side-scattered light in each dimension is adjusted to distribute the array of signals from the cells across the channels available for analysis in a manner well known to one skilled in the art. Under these circumstances a characteristic pattern, or scattergram, is observed. Analysis of blood samples reveals three major cell types in the scattergram, namely, monocytic cells, lymphocytes and granulocytes, each of which has distinguishable light scattering characteristics. The monocytic cell region, the granulocytic cell region and the lymphocytic region of the scattergram are gated so that cells which are classified as monocytes, granulocytes or lymphocytes can be analyzed further or collected by flow sorting.

Further analysis is carried out by staining the cells with fluorescent-coupled monoclonal antibodies or by subjecting the cells to in situ hybridization with fluorescent-coupled oligonucleotide probes. Under these conditions cells that have particular light scattering properties are also analyzed for the presence of fluorescence. When fluorescent-coupled antibodies are used, control experiments are performed using isotypically matched control monoclonal antibodies. When fluorescent-coupled oligonucleotide probes are used controls consist of oligonucleotide sequences unrelated to mammalian sequences.

Collected samples are deposited on one or more slides, with no more than 10,000 cells deposited on any single slide; care is taken that deposited cells form a monolayer such that the concentration of cells on the slide is low enough so that the cells do not overlap one another. At other times the cells are collected into microfuge tubes and fixed in suspension as described elsewhere.

A Coulter, Profile II, flow cytometer (Coulter, Hialeah, Fla.) may be used to detect nucleic acids within fetal cells, using a photo-multiplier-tube-1 (PMT-1) setting of 1100 and a PMT-3 setting of 900. Color compensation, PMT-1 minus PMT-3, may be 15%. An Epics, Elite, system may be used to sort fetal cells from a specimen, e.g., of maternal blood.

The present invention permits the use of flow cytometry for analysis and sorting of fetal cells based on the properties of the cells to scatter light in a forward direction and to the side.

Preferably, flow sorting is used after maternal red blood cells have been removed from the specimen to be analyzed. In the examples that follow a preferred amount of blood is collected. As illustrated in Examples 22 through 28 twenty milliliters (20 ml) of peripheral blood from a pregnant women of 10–20 weeks gestational age is collected in Vacutainer tubes containing EDTA. Also illustrated in those examples, is the separate collection of 1–5 ml of an umbilical cord blood sample from the birth of a male child in Vacutainer tubes containing EDTA. The blood-type of the maternal blood sample and the umbilical cord blood sample were determined. Only samples which had the same blood-type were used. The total number of nucleated red blood cells ("nRBC") and the number of nRBCs which contain the fetal hemoglobin mRNA ("F+") were determined, as illustrated in the examples, using the preferred amount of 20 μl of cord blood and the detection HbF system.

Separation of Fetal Nucleated Erythrocytes from mixed Adult and Cord Blood

1. Magnetic bead method:

Magnetic beads coated with anti-CD45 antibodies are added to the cells and the cells allowed to react. The magnetic beads bind mono-nuclear cells, lymphocytes and granulocytes all of which bear CD45 on their surfaces. The magnetic beads are then removed with a magnet and the unreacted cells in the supernate recovered. Hoechst dye 33258 is added as a nuclear counterstain. Examination of these cells by flow cytometry shows that they scatter light in the characteristic manner expected of mono-nuclear cells.

2. Flow Cytometer Method:

The cells are analyzed and sorted on a flow sorter and the cells with light scatter properties of monocytes, granulocytes and lymphocytes are collected. Different types of fetal cells are found to scatter light in characteristic ways. E.g., trophoblasts are found to have characteristic comparable to adult granulocytes whereas the light scattering characteristics of nucleated fetal erythrocytes are comparable to adult monocytes. Fetal leukocytes have light scattering characteristic similar to those of their adult counterparts. Cells with the light scattering properties of interest are collected and are deposited on one or more slides, so that deposited cells form a monolayer.

In examples 22 through 28 the separation of fetal cells from mixed maternal and cord blood is illustrated. These examples apply a fluorescence activated cell sorter to perform flow cytometry and identification of the fetal cells is achieved by using a system to test the fetal cells for the presence of HbF mRNA and X and Y chromosomes. The examples describe a variety of separation systems and vary the timing and frequency of the use of the system to test and detect fetal cell markers and chromosomes.

When fluorescein is the probe dye, the dye is excited with light having a wavelength 488 nm and the fluorescent emitted light is measured. For the emitted light detected by PMT-1, a 540 bandpass filter is used; i.e., only light with a wavelength between 520 nm and 560 nm is allowed to pass. The filter for PMT-3 is a 635 long pass filter; i.e., it allows any light over 635 nm wavelength to pass.

A marker may be used to define the cell as a fetal erythrocyte. For example, antibodies to representative fetal cell markers may be used, such as: (1) cytokeratin, (2) β-subunit of chorionic gonadotrophin, (3) fetal hemoglobin protein, (4) chorionic somatomammotropin protein (placental lactogen), (5) pregnancy-specific β-glycoprotein, and (6) α-fetoprotein. Various labeled antibodies to cytokeratin are available. These include CAM 5.2 from Becton Dickinson, Catalog No. 92-0005; and anti-cytokeratin 18-FITC from Sigma Chemical Company, Catalog No. F-4772 (antibody to cytokeratin 18). Most preferably, the antibody to cytokeratin is labeled with a fluorescent moiety.

Even more preferably, fetal-cell-specific RNA sequences are used as fetal cell markers. Such sequences are transcripts of, e.g., the fetal hemoglobin gene, the cytokeratin gene, the β-subunit of chorionic gonadotrophin gene, the chorionic somatomammotropin gene (placental lactogen), the pregnancy-specific β-glycoprotein genes, one or more embryonic hemoglobin genes or the α-fetoprotein gene. The sequences of these genes and others may be obtained from the Genetic Sequence Data Bank, GenBank, version 69.0. The loci of these sequences are provided in Table 9. A DNA probe, or population of probes, embodying any of these sequences is synthesized as an oligodeoxynucleotide using a commercial DNA synthesizer such as Model 380B from Applied Biosystems, Inc. Foster City, Calif., using reagents supplied by that company. Probes may be comprised of the natural nucleotide bases or known analogues of the natural nucleotide bases, including those modified to bind labeling moieties.

The novel methods of identifying fetal cells in a specimen using density gradient centrifugation utilize density gradient medium. Most preferably, the density gradient medium is colloidal polyvinylpyrrolidone-coated silica (e.g. Percoll), Nycodenz, a nonionic polysucrose (Ficoll) either alone or with sodium diatrizoate (e.g. Ficoll-Paque or Histopaque), or mixtures thereof. The density of the reagent employed is selected to preferentially separate the fetal cells of interest from other blood components.

The present invention permits detection of genetic abnormalities using a minimum number of fetal cells. Fetal cells may be obtained by amniocentesis, chorionic villi sampling or other standard methods known in the art. In one embodiment of the present invention, however, fetal cells are isolated from maternal peripheral blood, avoiding the invasion of the uterine cavity and thus precluding injury to the mother or fetus. In another embodiment of the present invention, fetal cells are isolated from a percutaneous sample of umbilical cord blood. The sensitivity of the present method permits drawing a smaller sample of umbilical cord blood than would need to be drawn using conventional fetal cell isolation and detection techniques. This sample is preferably 1–2 ml, but optionally as little as 0.2 ml.

Concentration of Fetal Nucleated Red Blood Cells in Maternal Blood

Figure 3A:
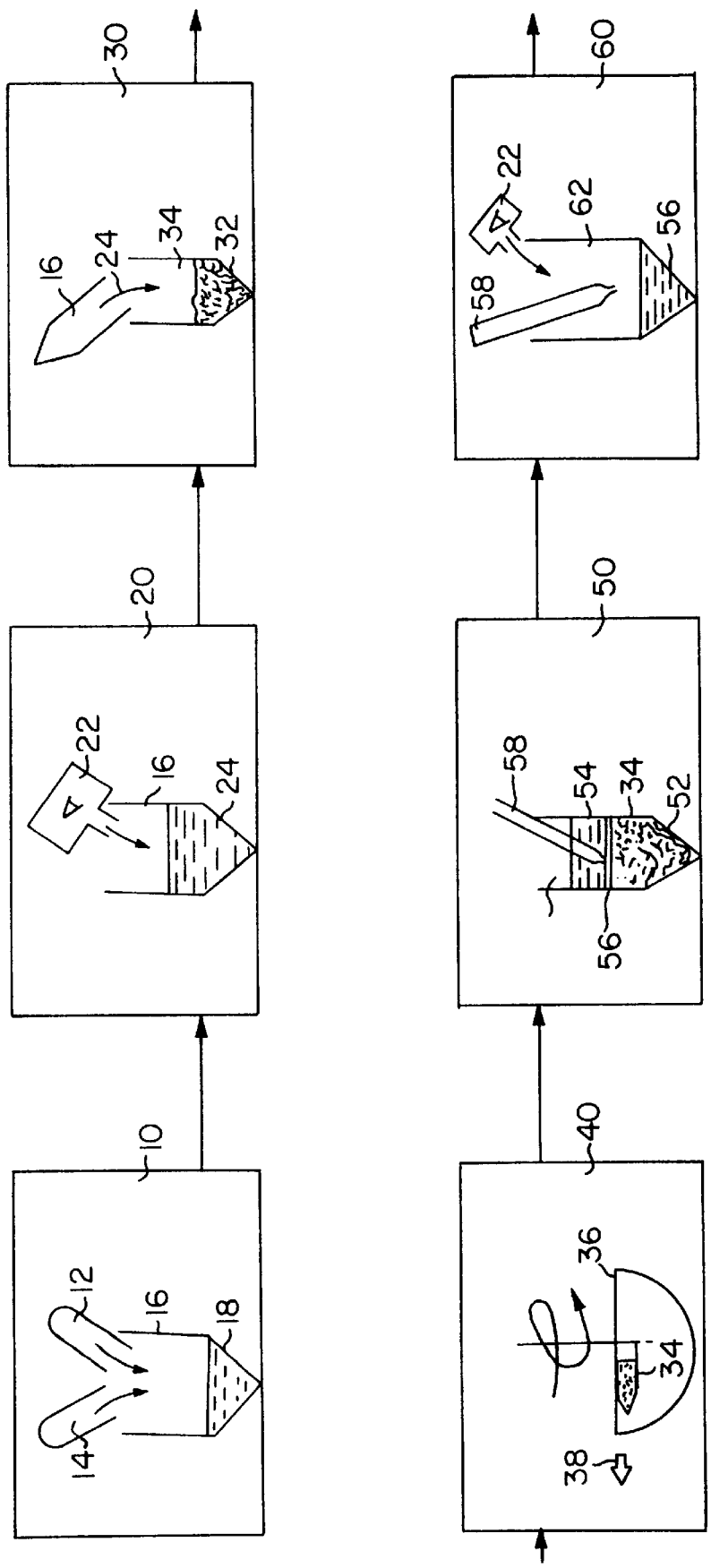
FIG. 3A shows a schematic representation of steps 10 to 60 of the technique preferably used to enrich fetal erythrocytes from maternal blood in accordance with the present invention.
Figure 3B:
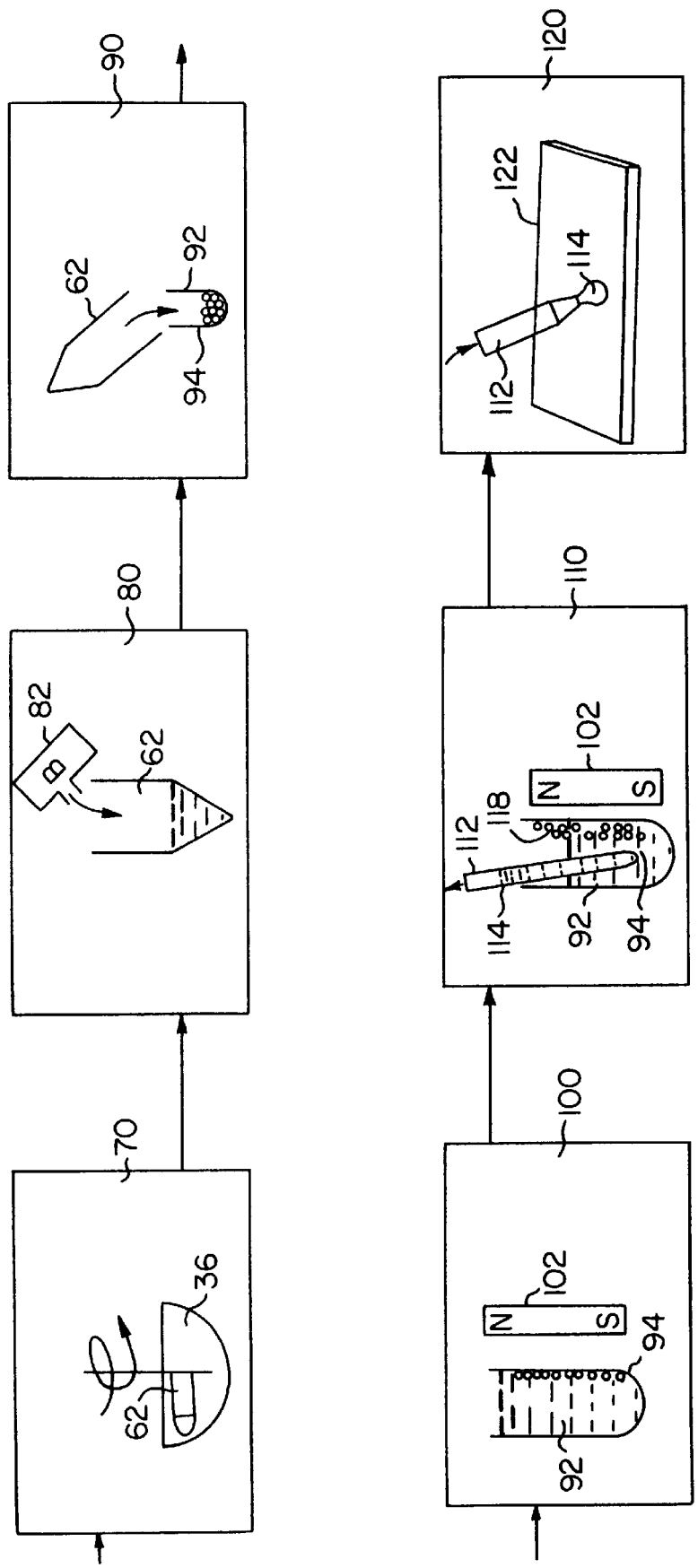
FIG. 3B shows a schematic representation of steps 70 to 120 of the technique preferably used to enrich fetal erythrocytes from maternal blood in accordance with the present invention.

An example of a separation of fetal nucleated red blood cells is shown in FIG. 3, consisting of parts 3A and 3B. Each step is schematically illustrated by a numbered box, and a component or container that appears in more than one step is identified by the same reference numeral.

In step 10, draw twenty ml of maternal peripheral blood, 18, e.g. into two conventional ten-ml EDTA anti-coagulation blood collection tubes, 12 and 14, e.g. Vacutainer tubes. Alternatively, ten ml of umbilical cord blood is drawn. The blood is transferred into a fifty-ml centrifuge tube, 16.

In step 20, the blood sample, 18, is mixed with fifteen ml of Cell Buffer A, 22, to form a buffered sample, 24. (See Exemplary Solutions, below.) Mix well.

In step 30, fifteen ml of a density-gradient separation reagent, 32, having a density of about 1.083, e.g. Histopaque 1083, is placed in a fifty-ml conical tube, 34, and up to twenty ml of the buffered sample, 24, is carefully layered on the top of the density separation reagent. The density separation reagent may have a density from about 1.075 to about 1.095, preferably between 1.08 and 1.09.

In step 40, the conical tube, 34, is centrifuged in a swinging-bucket rotor, 36, at 700×g for thirty minutes at room temperature. Arrow, 38, shows the direction of centrifugal force being applied to tube, 34, as illustrated. If two containers of blood sample were provided initially, then prepare and process a second density separation tube for the remaining twenty ml of diluted blood, repeating steps 30 and 40 as to the second tube. If the sample is umbilical cord blood, there would be only one such tube.

In step 50, aspirate off and discard the top serum/buffer layer, 54. Discard this waste. The buffy-coat, 56, is the interface layer at the top of the density separation reagent 52, which contains both maternal and fetal white blood cells, nucleated red blood cells, and erythroblasts. Collect the buffy-coat, 56, by pipette, 58, and transfer to a fresh fifty-ml conical tube, 62. If more than one tube, 34, of density separation material were prepared for a single patient, combine all interface layers, 56, into a single fifty-ml conical tube, 62.

In step 60, wash the collected cell layer with Cell Buffer A, 22, by adding Cell Buffer A to the cells to make the volume forty-five ml.

In step 70, pellet the cells in tube, 62, by centrifugation at 1000 rpm for ten minutes at room temperature.

In step 80, resuspend the cells, this time in one ml of Cell Buffer B, 82.

For step 90, prepare one hundred $\mu$l of anti-CD45 magnetic beads, 94, in a 2-ml microcentrifuge tube, 92, using aseptic technique as follows. (This preparation of the beads is not shown diagrammatically.) Wash the beads by adding 1.4 ml of Cell Buffer A, 22, using a magnet to retain the beads on the side of the tube. Let the tube sit undisturbed for 5 minutes. Carefully remove the wash solution with a pipette. Remove the magnet. As shown in the diagram for step 90, add to the tube, 92, the resuspended cells in tube, 64, from step 70. Incubate at room temperature for ten minutes, mixing gently.

In step 100, apply a magnet, such as a magnetic support block illustrated diagrammatically as magnet, 102, to retain the beads, 94, against the side of the tube, 92.

In step 110, remove and collect the liquid by pipette, 112. The cell suspension, 114, in pipette, 112, contains the fetal cells. The cellular material, 118, that remains with the beads, 94, primarily contains maternal leukocytes.

Step 120 diagrammatically represents the transfer of the cell suspension, 114, onto a microscope slide, 122, from pipette, 112. Such a transfer would generally be done by pipette. Alternatively, the washed fetal cell suspension may be transferred to a fresh tube (not shown), if hybridization in suspension is to be performed.

Alternatively, instead of using a bead having, for example, anti-CD45 bonded thereto (direct negative selection), one may react the specimen with anti-CD45 in solution and then remove the leucocytes, which have entered into an antigen-antibody ligand with the anti-CD45, by any means which separates such an antibody, and particularly by an antibody to an epitope of the CD45 molecule (indirect negative selection). Where the anti-CD45 is a mouse antibody, such a ligand-forming antibody may be, for example a sheep-anti-mouse-IgG antibody bonded to substrate that is generally solid or otherwise able to facilitate removal of the ligand complex from solution, such as an antibody-coated magnetic bead, the coated well of a container, etc.

Detection of Genetic Abnormalities

The genetic abnormalities detected by the present invention may be deletions, additions, amplifications, translocations or rearrangements.

For example, a deletion may be identified by detecting the absence of hybridizable binding of the probe to a target sequence. To detect a deletion of a genetic sequence, a population of probes are prepared that are complementary to the nucleic acid sequence that is present in a normal fetal cell but absent in an abnormal one. If the probes hybridize to the sequence in the cell being tested, then the sequence is detected and the cell is normal as to that sequence. If the probes fail to hybridize to cellular nucleic acid, then the sequence is not detected in that cell and the cell is designated as abnormal, provided that a control sequence, such as the X chromosome, is detected in that cell.

An addition may be identified by detecting binding of a labeled probe to a polynucleotide repeat segment of a chromosome. To detect an addition of a genetic sequence, such as an insertion in a chromosome or a karyotypic abnormality such as the trisomy of Chromosome 21 which indicates Down's Syndrome, a population of probes are prepared that are complementary to the genetic sequence in question. Continuing with the Down's Syndrome example, if the probes complementary to Chromosome 21 hybridize to three appearances of the Chromosome 21 sequence in the cell, then three occurrences of the Chromosome 21 sequence will be detected and indicate the Down's Syndrome trisomic condition. If the detection means is a fluorescent dye, for example, then three distinct points of fluorescence visible in each cell will indicate the trisomy condition.

As illustrated in Example 14, when an amplification of a particular DNA fragment is present, there is an increase in the intensity of the signal from a labeled probe for the sequence which is subject to amplification. Using any of a number of image analysis systems, this signal is quantified and compared to normal controls to determine whether or not a particular amplification mutation is present.

A translocation or rearrangement may be identified by several methods. For example, a labeled first probe may be bound to a marker region of a chromosome that does not translocate. A labeled second probe is then bound to a second region of the same chromosome (for a rearrangement) or a second chromosome (for a translocation) and subsequently binding of the first and second probes is detected. Alternatively, a translocation may be identified by first binding a labeled probe to a marker region of a polynucleotide section of a chromosome that translocates or rearranges. Subsequently, binding of the labeled probe is detected.

For example, to detect a translocation, a marker for the chromosome in question is identified, and a population of probes are prepared that hybridize to it. They are marked with a detectable label, such as a dye that fluoresces at a particular wavelength. The sequence that translocates or rearranges in the abnormality being tested for is also identified, and second population of probes are prepared that identify it. The members of the second population of probes are marked with a distinguishably different label, such as a dye that fluoresces at a different wavelength from the first series of labeled probes. In situ hybridization is performed using both populations of probes, and the results of hybridization by each of the probe populations are compared. If the first and second labels are coincident on virtually all cell samples, no translocation has taken place. If the first label is found not to coincide with the second label on a significant fraction of samples, then a translocation or rearrangement has taken place. See, e.g., F. Speleman, Clinical Genetics 41(4):169–174 (1992); J. W. Gray, Progress in Clinical & Biol. Res. 372:399–411 (1991).

Hybridization Fixative

Ethanol, e.g. 80% ethanol/water (v/v), is desirably used as a fixative during preparation of the cells for in situ hybridization. Other useful precipitation fixatives include acetic acid, methanol, acetone, and combinations thereof, for example ethanol/methanol mixture 3:1. Other useful fixatives will be obvious to one skilled in the art. Fixatives and hybridization of fixed cells, in general, are discussed in U.S. Pat. No. 5,225,326. Fixatives should provide good preservation of cellular morphology, should preserve and maintain accessibility of antigens, and promote a high hybridization efficiency. Some salts and extreme temperatures, such as waving a slide over a flame, may also function as fixatives.

The fixative may contain a compound which fixes the cellular components by cross-linking these materials together, for example, paraformaldehyde, glutaraldehyde or formaldehyde. Cross-linking agents, while preserving ultrastructure, often reduce hybridization efficiency by forming networks trapping nucleic acids and antigens and rendering them inaccessible to probes and antibodies. Some cross-linking agents also covalently modify nucleic acids, preventing later hybrid formation.

Hybridization Solution Components

The hybridization solution may typically comprise a chaotropic denaturing agent, a buffer, a pore-forming agent, a hybrid stabilizing agent. The chaotropic denaturing agents include formamide, urea, thiocyanate, guanidine, trichloroacetate, tetramethylamine, perchlorate, and sodium iodide. Any buffer which maintains pH at least between about 6.0 and about 8.5 and preferably between 7.0 and 8.0 may be utilized.

The pore-forming agent is, for instance, a detergent such as Brij 35, Brij 58, sodium dodecyl sulfate, CHAPS, Tween, Sarkosyl or Triton X-100. Depending on the location of the target nucleic acid, the pore-forming agent is chosen to facilitate probe entry through plasma, nuclear membranes or cellular compartmental structures. For instance, 0.05% Brij 35 or 0.1% Triton X-100 will permit probe entry through the plasma membrane but not the nuclear membrane. Alternatively, sodium deoxycholate will allow probes to traverse the nuclear membrane. Thus, in order to restrict hybridization to the cytoplasmic nucleic acid targets, nuclear membrane pore-forming agents are avoided. Such selective subcellular localization contributes to the specificity and sensitivity of the assay by eliminating probe hybridization to complementary nuclear sequences when the target nucleic acid is located in the cytoplasm. Agents other than detergents, such as fixatives or salts, may serve this function.

Hybrid stabilizing agents such as salts of monovalent and divalent cations are included in the hybridization solution to promote formation of hydrogen bonds between the nucleotide sequences of the probe and the complementary nucleotide sequences of the target nucleic acid. Preferably, sodium chloride at a concentration from 0.15M to 1M is used. In order to prevent non-specific binding of nucleic acid probes, nucleic acids unrelated to the target nucleic acids may desirably be added to the hybridization solution.

Many types of solid supports may be utilized to practice the invention. Supports which may be utilized include, but are not limited to, glass, Scotch tape (3M Corporation, St Paul Minn.), nylon, Gene Screen Plus (New England Nuclear, Boston Mass.) and nitrocellulose. Most preferably, glass microscope slides are used. The use of these supports and the procedures for depositing specimens thereon is obvious to those of skill in the art. The choice of support material will depend upon the procedure for visualization of cells and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

In one embodiment of the process, the target cell is immobilized on a solid surface, preferably a glass slide. In another embodiment, the target cell is suspended in liquid during the entire process and not immobilized on a solid surface. Use of conventional flow cytometry instruments is especially facilitated with the present invention. ps Blocking Background Effects The process comprises contacting the cell with a solution containing a probe capable of binding to a target molecule in or on the cell so that the probe with a reporter group attached binds to the target molecule and becomes cell-bound. To reduce the background the cell is treated with a solution comprising a structural analogue of the reporter group. Analysis is achieved by performing one or more steps that will detect the reporter group on the probe bound to the cell but that will not detect the analogue bound to the cell matrix.

In this process the analogue of the reporter group may be added before, together with or after the probe bound reporter group. Preferably, the probe and the analogue are included in the same solution.

In a subgeneric aspect of the invention, the reporter group is a cyclic compound. In a further subgeneric aspect of the invention, the cyclic group contains an unsaturated bond. In a still narrower subgeneric aspect of the invention, the cyclic group is an aromatic compound. It is preferred that, on a molar basis, the analogue is in excess as regards the reporter group; it is highly preferred that there be at least ten times as much analogue as reporter group.

The analogue competes with the reporter group for non-specific binding sites. In the case of aurintricarboxylic acid (ATA) used in conjunction with a nucleic acid probe, an additional mechanism may involve ATA binding to the active site of proteins that would bind the reporter group. It is preferred that the analogue is selected so that it retains most or all of the structural features of the reporter group. The analogue may additionally have structural features not present in the probe.

Preferably, the analogue should be able to permeate a cell or virus. In the case of analogues that are aurin derivatives (rosolic acid derivatives), it is preferred that the analogues have, in addition to ATA, a polar functional group such as a —$CO_2$, —$NH_2$, —OH, or —$SO_3$ group, on an aromatic group; examples are chromoxane cyanine R and Chrome Azurol S. A subgroup of preferred analogues are those that block the $NH_2$ groups on lysines.

In the preferred embodiments, multiple probes for multiple target sequences are simultaneously hybridized. For example, probes for HbF mRNA and for human chromosome 21 are desirably included in the contacting step, and the reporter group on the probes for HbF mRNA is detectably different from the reporter group on the probes for chromosome 21.

Detection of Probe Moieties

Fluorescent reporter groups are detected by exciting the reporter group with a higher energy light and then detecting the emission of some of the absorbed energy as a lower energy light.

Chemiluminescent reporter groups are detected by allowing them to enter into a reaction, e.g., an enzymatic reaction, that results in energy in the form of light being emitted.

Other reporter groups, e.g., biotin, are detected because they can bind to groups such as streptavidin which are bound, directly or indirectly, to enzymes, e.g., alkaline phosphatase or horseradish peroxidase that can catalyze a detectable reaction.

Fluorescent groups with which the process of this invention can be used include fluorescein, coumarin, rhodamine, rhodamine derivatives including Texas Red, and phycoerythrin.

Chemiluminescent groups with which the process of this invention can be used include isoluminol (or 4-aminophthalhydrazide; see catalogs of Aldrich Chemical Company or Molecular Probes, Inc.).

In one preferred embodiment of the process, when the reporter group is fluorescein, detection is achieved by measuring light emitted at wavelengths between about 520 nm and 560 nm (especially at about 520 nm), most preferably where the excitation wavelengths is about or less than 520 nm.

A preferred embodiment of the fluorimetric process further comprises a wash step prior to the detection step. A wash step can be performed by centrifuging the cell out of the solution in which it is suspended, then suspending it in a wash solution, and then centrifuging it out of the wash solution. A wash solution is generally a probe-free solution.

In a particular embodiment of the process, the solution that is used comprises a probe (containing a reporter group), an analogue of the reporter group, a free radical scavenger and a fixative.

A fluorescent probe that binds to a target molecule is preferably one which binds to that target with high specificity. Preferably, a fluorescent probe is fluorescent dye covalently attached to a nucleic acid molecule, antibody or other molecule capable of binding specifically to a target molecule.

If an analogue is added to the cocktail, its preferred concentration is from 0.01% to 0.5% w/v (especially about 0.05 to 0.01%).

Kit Embodiments of the Invention

In one aspect, the invention is a kit for the detection of nucleic acids within a fetal cell in a specimen. Such a kit may include a solution containing a fixation/hybridization cocktail and one or more labeled probes. For example and not by way of limitation, this solution may contain 50 mM guanidinium isothiocyanate, 25–40% formamide, 31% PEG, 0.4M DTT, 15×Ficoll/PVP, 50 2 mM EDTA, 1 mg/ml salmon sperm DNA, 50 mM Tris-acetate (pH 7–8), about 5% Triton X-100, and about 20 μg/ml of a synthetic oligonucleotide probe directly labeled with a reporter molecule. This solution and the probes would have measurable predefined and identified characteristics and reactivities with cells and target sequences. Such a kit would also provide means and instructions for performing the hybridization reaction of the invention.

In an alternative embodiment, the kit may include: a second detectable reporter system which would react with the probe or the probe-target hybrid. Concentrated stock solution(s) to be used directly or to be diluted sufficiently to form wash solution(s). Any mechanical components which may be necessary or useful to practice the invention such as a solid support (e.g., a microscope slide), an apparatus to fix cells to the support, or a device to assist with any incubation or washing of the specimens. Such a kit could also include a photographic film or emulsion with which to the record results of assays carried out with the invention.

Another aspect of the present invention provides a kit for the detection of fetal hemoglobin within a specimen without the removal of maternal blood cells. A preferred version of this kit contains means for detecting the HbF mRNA of fetal cells. The kit would also provide media for mounting slides of capillary blood smears, e.g. Slide Mount A, Slide Mount B and Slide Mounting Solution. Further, Wash Concentrate A, Wash Concentrate B and Fetal Hemoglobin Assay Solution would be provided. The concentrates mentioned herein would be diluted in use to approximately the solution concentrations stated below in Exemplary Solutions.

Yet another aspect of the present invention would be a kit to enrich and detect fetal cells within a blood specimen, e.g. maternal or umbilical cord blood. Such a kit may contain one or more reagents to prepare a density gradient that concentrates fetal cells. Labeled antibodies to detect or separate fetal cells and/or probes specific for fetal cell mRNA (preferably fetal hemoglobin mRNA), and means and instructions for performing fetal cell enrichment.

Again, an alternative kit may contain one or more antibodies, desirably bound to a solid support and preferably bound to magnetic beads, to positively or negatively concentrate fetal cells within the specimen, preferably including an anti-CD45 antibody for negative selection of fetal erythrocytes, probes specific for fetal cell mRNA, means and instructions for performing fetal cell enrichment using density gradient centrifugation or flow cytometry, and optionally one or more reagents to prepare a density gradient that concentrates fetal cells.

Advantageously either such of the two kits described immediately above may also be provided with means for detecting one or more target nucleic acid sequences within the fetal cells, by including a second detectable reporter system which would react with the probe or the probe-target hybrid, concentrated stock solution(s) to be used directly or to be diluted sufficiently to form wash solution(s), and, optionally, any mechanical components which may be necessary or useful to practice the present invention such as a solid support (e.g., a microscope slide), an apparatus to affix cells to said support, or a device to assist with any incubations or washing of the specimens, and a photographic film or emulsion with which to record results of assays carried out with the present invention.

Such a kit would optionally provide reagents and materials for use in an automated system for the performance of any of the methods of the present invention.

Tables 1 and 2 contain the abbreviations and common names for various compounds and dyes mentioned herein.

TABLE 1

Abbreviations and Common Names of Compounds and Dyes

| Abbreviation or Common Name | Compound |
|---|---|
| Tempo | 2,2,6,6-tetramethylpiperidine-N-oxyl [CAS # 2564-83-2] |
| EDTA | ethylene diamine tetraacetic acid |
| DMF | dimethyl formamide |
| DMSO | dimethyl sulfoxide |
| DTT | dithiothreitol |
| PVP | polyvinylpyrrolidone |
| PEG 4000 | polyethylene glycol (ca. 4000 Mol. Wt.) |
| PBS | phosphate-buffered saline solution |
| ATA | aurintricarboxylic acid [CAS # 4431-00-9] |
| CHAPS | 3-[(3-cholamidopropyl)-dimethylammonio]-1-propane-sulfonate [CAS # 75621-03-3] |
| photobiotin | N-(4-azido-2-nitrophenyl)-N'-(3-biotinylaminopropyl)-N'-methyl-1,3-propanediamine [CAS # 96087-37-5] |
| Ficoll | nonionic polysucrose (Pharmacia) |
| Histopaque 1083 | aseptically filtered solution containing Ficoll nonionic polysucrose (type 400) and sodium diatrizoate, density 1.083 |
| Percoll | colloidal PVP-coated silica [CAS # 65455-52-9] |
| Nycodenz | 5-(N-2,3-dihydroxypropylacetamido)-2,4,6-triiodo-N,N'-bis(2,3 dihydroxypropyl)isophthalamide [CAS # 66108-95-0] |
| Tween | polyoxyethylene sorbitan salts of fatty acids |
| Sarkosyl | N-lauroylsarcosine, sodium salt [CAS# 7631-98-3] |
| Triton X-100 | octyl phenoxy polyethylene glycol (a polyoxyethylene ether) [CAS # 9002-93-1] |
| Brij 35 | polyoxyethylene 23 lauryl ether [CAS # 9002-92-0] |
| Brij 58 | polyoxyethylene 20 cetyl ether [CAS # 9004-95-9] |
| Tris | tris(hydroxymethyl)aminomethane [CAS # 77-86-1] |
| isoluminol | 4-aminophthalhydrazide [CAS # 3682-14-2] |
| APTO | 3-aminopropyltriethoxysilane [CAS # 919-30-2] |
| DAPI | 4',6-diamidino-2-phenylindole hydrochloride [CAS # 28718-90-3] |
| BCIP | 5-bromo-4-chloro-3-indolyl phosphate [CAS # 102185-33-1] |
| digoxigenin | [CAS # 1672-46-4] |

TABLE 2

| Dye abbreviations Dye Number | Actual Dye Name | Abbreviation |
|---|---|---|
| 12 | Naphthol Blue Black | Naphthol Bl. Blk. |
| 13 | Palatine Fast Black WAN | Palatine F-B WAN |
| 20 | Sulforhodamine 101 hydrate [CAS # 60311-02-6] | Sulforhodamine 101 |
| Texas Red | Sulforhodamine 101 acid chloride [CAS# 82354-19-6] | |

TABLE 2-continued

Dye abbreviations

| Dye Number | Actual Dye Name | Abbreviation |
|---|---|---|
| Direct Blue 53 | Evans Blue [CAS # 314-13-6] | — |
| Fluorescein isothiocyanate | | FITC |
| Hoechst 33258 | 2'-[4-hydroxyphenyl]-5-[4-methyl-1-piperazinyl]-2-5'-bi-1H-benzimidazole trihydrochloride [CAS # 23491-45-4] | |
| Natural Black 1 | Hematoxylin [CAS # 517-28-2] | — |
| Acid Red 91 | Eosin B [CAS # 548-24-3] | — |
| Sigma 840-10 | Nitroblue Tetrazolium | NBT |
| PE | Phycoerythrin | |
| Cy3 | FluoroLink Cy3 Fluorescent Dye, a fluorescent cyanine dye (Biological Detection Systems, Inc., 955 William Pitt Way, Pittsburgh, PA) | |
| Cy5 | FluoroLink Cy5 Fluorescent Dye, a fluorescent cyanine dye (Biological Detection Systems) | |

Exemplary Solutions

The following solutions may be used in the performance of the present invention.

Cell Buffer A: (as diluted for use): 0.8% BSA, 0.1% dextrose, 0.1% sodium azide in PBS.

Cell Buffer B: (as diluted for use): 2% BSA, 0.1% dextrose, 0.1% sodium azide in PBS.

Fixation solution: 4 volumes ethanol, 5 volumes of PBS, 1 volume of glacial acetic acid.

Hybridization cocktail: 5×SSC (SSC has the following composition: 0.15M NaCl, 0.15M sodium citrate, pH 7.0. 2×SSC is composed so that upon a 1:1 dilution with water, SSC would be produced; 5×SSC is composed so that upon a 1:5 dilution with water, SSC would be produced; 10×SSC is composed so that upon a 1:10 dilution with water, SSC would be produced); 30% formamide (v/v); 3% Triton X-100 (v/v); 0.4M guanidinium isothiocyanate; 0.16M sodium phosphate (pH 6); 15×Ficoll/PVP; 1 mg/ml sheared salmon or herring sperm DNA; 10 mM EDTA; 25 mM DTT; 31% PEG 4000.

Hybridization Temperature: For hybridization cocktails used with a nucleic acid probe, the temperature for the hybridization reaction is within the range of about 20° C. and about 90° C., preferably about 37° C. and about 85° C., and most preferably about 40° C. and about 46° C. The time of the hybridization reaction is between 5 minutes and 16 hours, and preferably is less than 4 hours. More preferably, the time of the hybridization reaction is less than 120 minutes, even more preferably less than 60 minutes. Most preferably, the reaction time is less than 30 minutes.

Wash Solution #1: has the following composition: 0.4M guanidinium isothiocyanate; 0.1% Triton X-100 (v/v); and 0.1×SSC in deionized water.

Wash Solution #2: has the following composition: 0.1% Triton X-100 (v/v) and 0.1×SSC in deionized water.

PBS: has the formula, 0.136M NaCl, 0.003M KCl, 0.008M $Na_2HPO_4 \cdot 7H_2O$, 0.001M $KH_2PO_4$.

Fluorescent-Coupled Antibodies: If a dye-labeled antibody is used as the probe, then the probe may be dissolved in PBS, possibly supplemented with bovine serum albumin (BSA), while it is allowed to react with target cells, preferably at a temperature in the range 4° C. to 34° C. The cells need not be fixed (e.g., when the antibody target is a cell-surface antigen), or may be fixed after the probe-target incubation is completed, or may be fixed prior to or during the probe-target incubation.

Mounting Solution: may be 50% PBS/50% glycerol (v/v), 0.1% 1,4-phenylenediamine (as an antifade) and 1 μg/ml of Hoechst 33258 or DAPI (dye).

Nucleotide Probes: The probes may be DNA or RNA or synthetic analogues to DNA or RNA. The probe is capable of binding to a complementary target cellular genetic sequence through one or more types of chemical bonds, usually through hydrogen bond formation. In general, the DNA or RNA probes may be composed of the bases adenosine, uridine, thymidine, guanine, cytosine, or any natural or artificial chemical derivatives thereof. The phosphate backbone is linked via ribose or deoxyribose, or an analog or derivative thereof. Nucleic acid probes can be prepared by a variety of methods known to those of skill in the art. The probes may be oligonucleotides synthesized with an Applied Biosystems Inc. (A.B.I.) DNA synthesizer Model 380 using the recommended A.B.I. reagents.

In the last stage of the synthesis, an aminohexyl phosphate linker is desirably attached to the 5' end of the probes for the fetal-cell-specific marker, and preferably to both the 5' and 3' ends of the probes for the other sequences to be detected, e.g. chromosomal sequences. The 5'- or 5', 3'- aminohexyl oligonucleotides are then respectively coupled to a selected dye and purified by HPLC. However, as illustrated in Examples below, even if only a single fluorescent label is attached to the probes, fluorescence may be detected by visual microscopy.

Purified single-stranded DNA probes may alternatively be produced by the use of single-stranded phage M13 or plasmid derivatives of this phage, or by reverse transcription of a purified RNA template.

Detection Systems

Detectable labels may be any molecule which may be detected. Commonly used detectable labels are radioactive labels including, but not limited to, $^{32}P$, $^{14}C$, $^{125}I$, $^{3}H$ and $^{35}S$. Biotin labeled nucleotides can be incorporated into DNA or RNA by nick translation, enzymatic, or chemical means. The biotinylated probes are detected after hybridization using avidin/streptavidin, fluorescent, enzymatic or colloidal gold conjugates. Nucleic acids may also be labeled with other fluorescent compounds, with immunodetectable fluorescent derivatives or with biotin analogues. Nucleic acid probes may also include any number of modified bases such as methylated bases, inosine and other naturally occurring or synthetic nucleotides. Nucleic acids may also be labeled by means of attaching a protein. Nucleic acids cross-linked to radioactive or fluorescent histone HI, enzymes (alkaline phosphatase and peroxidases), or single-stranded binding (ssB) protein may also be used. To increase the sensitivity of detecting the colloidal gold or peroxidase products, a number of enhancement or amplification procedures using silver solutions may be used.

An indirect fluorescent immunocytochemical procedure may also be utilized (Rudkin and Stollar (1977) Nature 265:472; Van Prooijen, et al (1982) Exp. Cell. Res. 141:397). Polyclonal antibodies are raised against RNA-DNA hybrids by injecting animals with poly(rA)-poly(dT). DNA probes are hybridized to cells in situ and hybrids are detected by incubation with the antibody to RNA-DNA hybrids.

Probes may be detectably labeled prior to addition to the hybridization solution. Alternatively, a detectable label may be selected which binds to the hybridization product. Probes may be labeled with any detectable group for use in practicing the invention. Such detectable group can be any material having a detectable physical or chemical property. Such detectable labels have been well-developed in the field of immunoassays, and in general, most any label useful in such methods can be applied to the present invention. Particularly useful are enzymatically active groups, such as enzymes (see Clin. Chem., 22:1243 (1976)), enzyme substrates (see British Patent Spec. 1,548,741), coenzymes (see U.S. Pat. Nos. 4,230,797 and 4,238,565) and enzyme inhibitors (see U.S. Pat. No. 4,134,792); fluorescers (see Clin. Chem., 25:353 (1979); chromophores; luminescers such as chemiluminescers and bioluminescers (see Clin. Chem., 25:512 (1979)); specifically bindable ligands; proximal interacting pairs; and radioisotopes such as $^3$H, $^{35}$S, $^{32}$P, 125I and $^{14}$C.

Probe Size, Population and Concentration The length of a probe affects its diffusion rate, the rate of hybrid formation, and the stability of hybrids. According to the present invention, small probes (15–200 bases, and preferably 15–100, most preferably 15–30) yield the most sensitive, rapid and stable system. A mixture of small probes as aforesaid which span the entire length of the target nucleic acid to be detected are desirably prepared. For example, if the target nucleic acid were 1000 bases long, up to about 40 "different" probes of 25 bases would be used in the hybrid solution to completely cover all regions of the target nucleic acid.

A particularly advantageous configuration of probes is to prepare a population of probes to a selected target sequence as follows: A first probe hybridizes to bases 1 to 25 of the sequence. A second probe hybridizes to bases 31 to 55 of the sequence. A third probe hybridizes to bases 61 to 85 of the sequence, and so on, wherein the beginning of each succeeding probe is spaced about 5 bases from the end of the preceding probe. It has been found that such a configuration wherein 5 bases are omitted between each 25-mer probe provides optimal hybridization results and signal, when employed in hybridizations in accordance with the present invention.

The concentration of the probe affects several parameters of the in situ hybridization reaction. High concentrations are used to increase diffusion, to reduce the time of the hybridization reaction, and to saturate the available cellular sequences. To achieve rapid reaction rates while maintaining high signal-to-noise ratios, probe concentrations of 0.005–100 µg/ml are preferable. Most preferable is use of probes at a concentration of about 0.01 µg/ml.

Detection of Specific Genetic Abnormalities

Among the genetic abnormalities that may be detected by the tests of the present invention are Down's Syndrome (trisomy 21), Turner's Syndrome (XO chromosomes), Klinefelter's Syndrome (XXY chromosomes), Edward's Syndrome (trisomy 18) and Patau Syndrome (trisomy 13).

The following examples are offered by way of illustration and are not intended to limit the invention in any manner.

EXAMPLES

Example 1

The Use of Chromosome-Specific Probes to Determine the Numerical Status of Specific Chromosomes in Amniocytes Preparation of Cells Two ml of amniotic fluid was diluted to 10 ml with PBS and centrifuged at 1200 rpm for 10 minutes. The resultant cell pellet was suspended in 1000 pi of ethanol and methanol (v:v, 3:1). Two hundred µl of sample was deposited on each slide by the cytospin method.

Preparation of Probes Several 25-base synthetic oligonucleotide probes were prepared from each of the DNA sequences listed in Table 3.

TABLE 3

| Probe Designation | Chromosome Detected | GenBank Locus Name |
|---|---|---|
| Alpha-centromeric repeat | X | HUMSATAX |
| Alpha-centromeric repeat | Y | HUMSATB |
| Alpha-centromeric repeat | 18 | HUMREPA84 |

Probe Synthesis & Labeling

The oligodeoxynucleotides were synthesized (Applied Biosystems, Inc. DNA Synthesizer Model 380B) using the recommended A.B.I. reagents, and in the last stage an aminohexyl phosphate linker was attached to the 5' end. The 5'-aminohexyl oligodeoxynucleotides were then coupled to a rhodamine dye from Molecular Probes, Inc. and purified by Waters HPLC using a baseline 810 chromatography work station.

Hybridization

For the hybridization procedure, the cells were deposited onto slides. Twenty to 25 µl of a hybridization cocktail consisting of 30% formamide, 5×SSC, 0.1M sodium phosphate buffer, pH 7.4, 100 µg/ml low molecular weight, denatured, salmon or herring sperm DNA, 10% (v/v) Triton X-100, 10% DMSO, 15×Ficoll/PVP, 0.4M guanidinium isothiocyanate, 10 mM DTT, and 0.025M EDTA and the probe, added at a concentration of 20 µg/ml. Denaturation and hybridization were carried out simultaneously by placing the slides in an incubator for 15 minutes at 85° C.

Three separate hybridization solutions were prepared. The first solution contained a probe for the X chromosome; the second, a probe for the Y chromosome; the third, a probe for chromosome 18.

Washing

Washing of the slides after the hybridization reaction is essential to eliminate background due to non-specific binding of the probe. Post-hybridization, the slides were placed in a Coplin jar to which was added 100 ml of the Wash Solution #1. The solution was agitated and held in this solution for 2 minutes. This wash solution was removed and Wash Solution #2 was added. This second wash solution was agitated for 5 seconds and poured off. The washing procedure with Wash Solution #2 was repeated six times. Then each specimen was mounted in 15 µl of Mounting solution placed on each slide.

Fluorescence Detection

Photomicrographs were taken on an Olympus BH10 microscope with fluorescence capabilities, using Kodak Ektachrome EES-135 (PS 800/1600) film, exposed, and push processed at 1600 ASA. A 30 to 60 second exposure time was consistently used, so that direct comparisons could be made between all photomicrographs taken.

Figures 1, 1B:
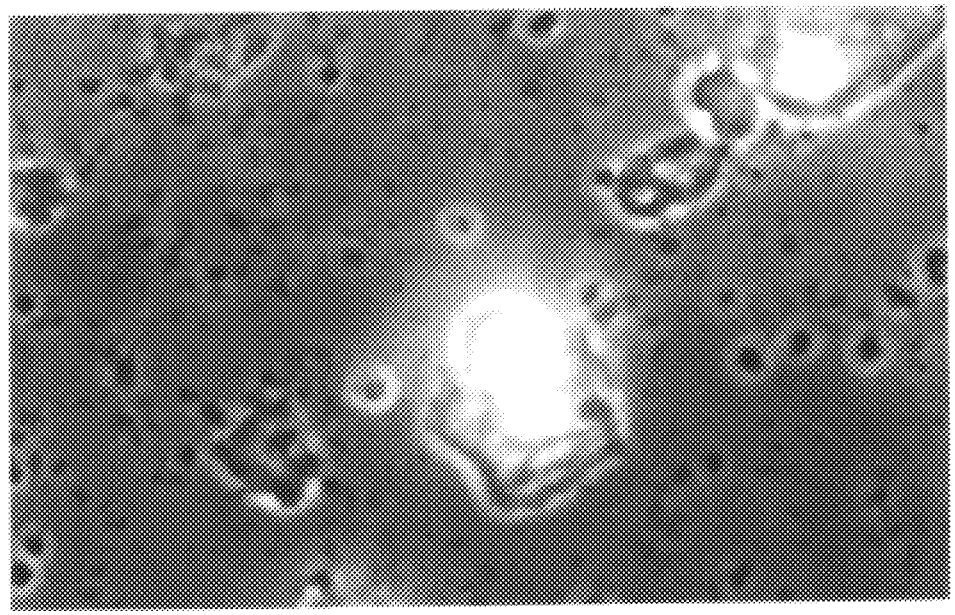
Figures 1, 1B, 2:
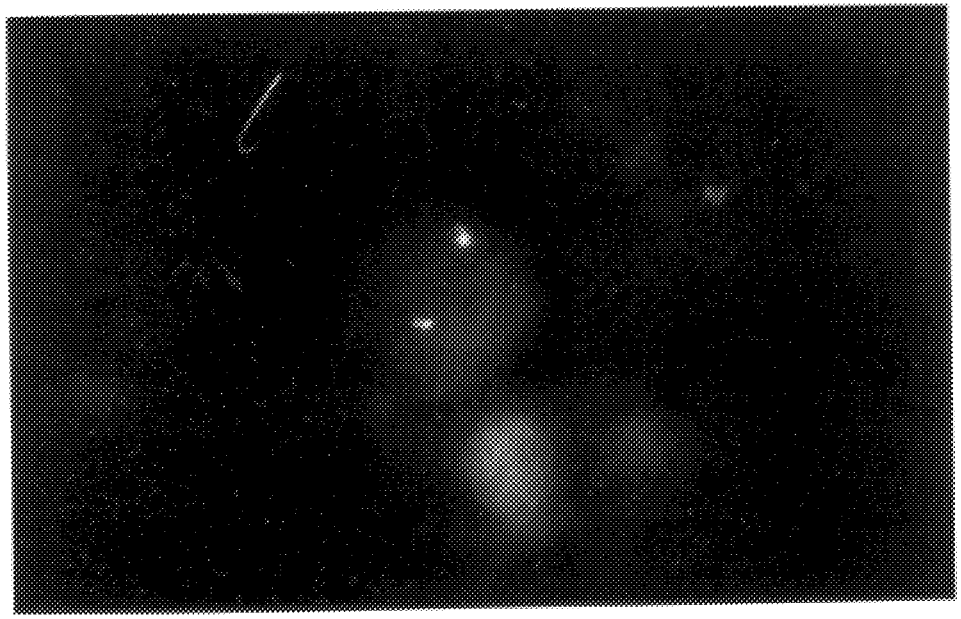
Figures 1, 1C:
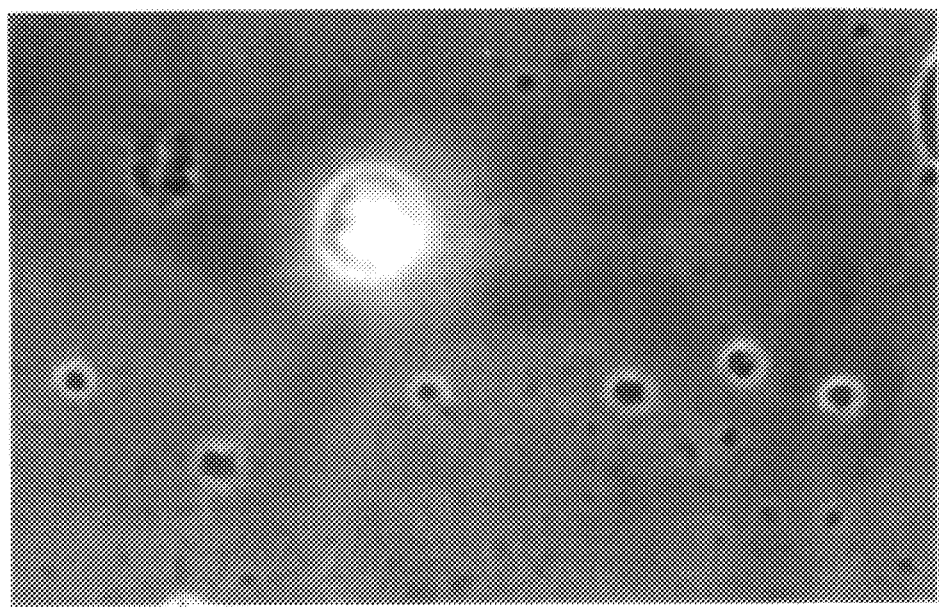
Figures 1, 1C, 2:

As shown in FIG. 1A, a single point of fluorescence (a "dot") is visible in the nucleus of male amniocytes when the Y probe was used. FIG. 1A: the top panel is a photograph (40× magnification) of two Hoechst stained nuclei while the bottom panel is the fluorescent photograph (100× magnification) of these same two cells. FIG. 1B shows a female amniocyte with 2 dots visible in the nuclei when the X probe was used: the top panel is a photograph of a Hoechst stained nuclei (40× magnification) while the bottom panel is the photograph of this same cell viewed with fluorescence (100× magnification). There are two dots in the nucleus when a probe for chromosome 18 was used (FIG. 1C). FIG. 1C: the top panel is a photograph of a Hoechst stained nucleus, while the bottom is a fluorescent view. Thus, there are the "normal" number of X, Y and 18 chromosomes present in these amniocytes.

Example 2

Simultaneous Detection of Numerical Status of X and Y Chromosomes in Amniocytes and in Peripheral Blood Mononuclear Cells Preparation of Cells Two ml of amniotic fluid was diluted to 10 ml with PBS and centrifuged at 1200 rpm for 10 minutes. The resultant cell pellet was suspended in 800 μl of ethanol and methanol (v:v, 3:1), Two hundred μl of the sample was deposited on each slide by the cytospin method. In addition, approximately 5,000 peripheral blood mononuclear cells obtained from a normal male were deposited on a slide by the cytospin method.

Preparation of Probes

Several 25-base synthetic oligonucleotide probes were prepared from each of the DNA sequences listed in Table 4.

TABLE 4

| Probe Designation | Chromosome Detected | GenBank Locus Name | Fluorescent Label |
|---|---|---|---|
| Alpha-centromeric repeat | X | HUMSATAX | Rhodamine |
| Alpha-centromeric repeat | Y | HUMSATB | Fluorescein |

Probe Synthesis, Labeling, Hybridization, Washing and Detection

These steps were performed as described in Example 1.

Results

Figures 1, 2A:
Figures 2, 2A:
Figures 1, 2B:
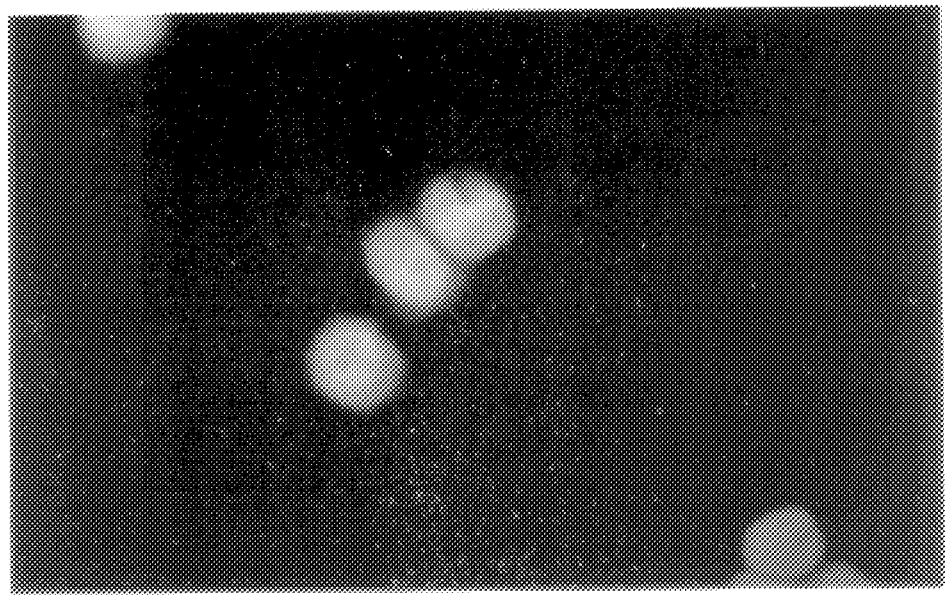
Figures 2, 2B:

In this experiment, the X chromosome probe was labeled with rhodamine while the Y chromosome probe was labeled with FITC, and both probes were added to the same hybridization cocktail and taken through the above procedure. In FIG. 2A, the top panel is a photograph of the Hoechst stained nucleus of an amniocyte and the bottom panel is a photograph of the fluorescence demonstrating one bright dot (X chromosome) and one bright dot (Y chromosome) in the nucleus. FIG. 2B is a photograph of three additional amniocytes as photographed in FIG. 2A.

Figure 2C:
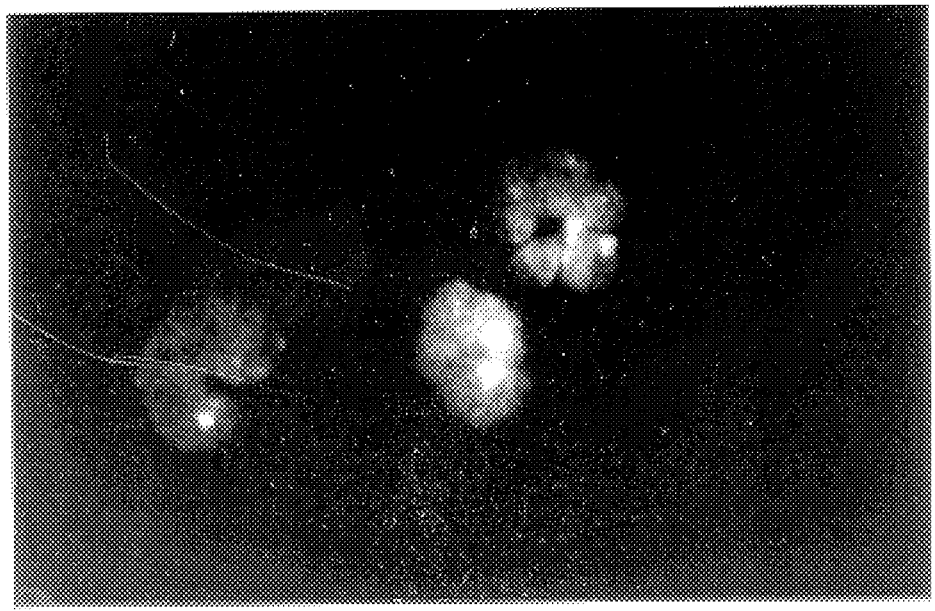
FIG. 2C shows the simultaneous detection of the X and Y chromosomes within white blood cells.
Figure 2D:
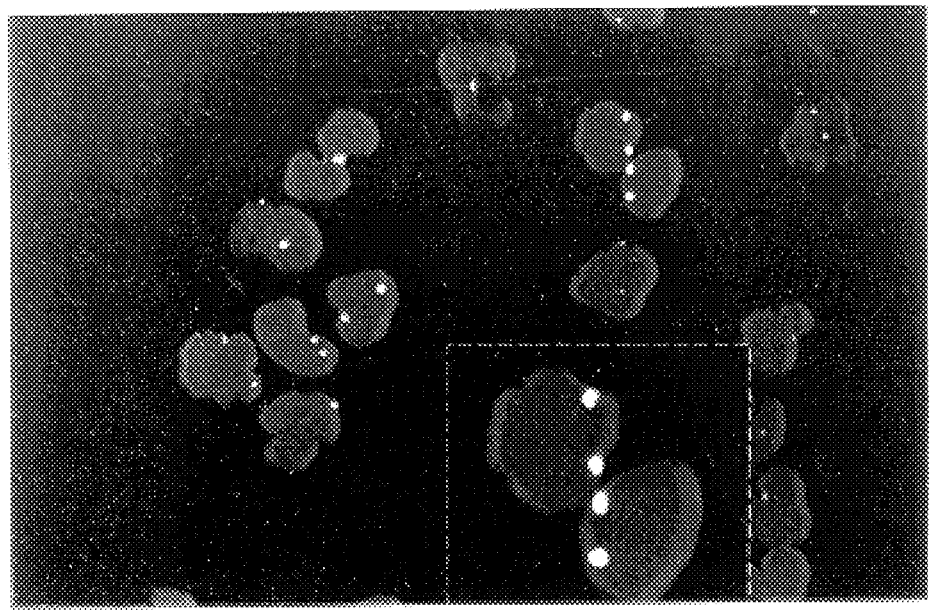
FIG. 2D shows the pseudo color representation of the detection of the X and Y chromosomes within the white blood cells shown in FIG. 2C.

FIG. 2C demonstrates the results obtained using this same hybridization cocktail and normal male peripheral blood mononuclear cells when the photograph is taken through a triple band (DAPI-FITC-rhodamine) filter set. This photograph again shows one bright dot and one bright dot for the X and Y chromosomes, respectively, on the Hoechst stained background. FIG. 2D is a photograph of a pseudo color representation of the cells in FIG. 2C using an image analysis system (BioScan Optimas™, Edmonds, Wash.).

Example 3

Use of Chromosome-Specific Probes to Determine the Number of Chromosomes in Embryos Prepared for In Vitro Fertilization or in Fetal Cells Obtained From Chorionic Villi Preparation of Cells Cells from non-viable embryos prepared for in vitro fertilization, cells from products of conception, and cells from chorionic villi, are accessed in a standard fashion, and deposited onto glass slides.

Preparation Of Probes

Several 25-base synthetic oligonucleotide probes are prepared from each of the DNA sequences listed below in Table 5.

TABLE 5

| Probe Designation | Chromosome Detected | GenBank Locus Name | Fluorescent Label |
|---|---|---|---|
| Alpha-centromeric repeat | X | HUMSATAX | Rhodamine |
| Alpha-centromeric repeat | Y | HUMSATB | Fluorescein |
| Alpha-centromeric repeat | 18 | HUMREPA84 | Coumarin |
| Alpha-centromeric repeat | 16 | HUMASATD | Rhodamine |
| Amyloid | 21 | HUMAMYB | Rhodamine |
| Collagen type IV | 13 | HUMCOL1A | Fluorescein |
| Human satellite DNA | 1 | HUMSAT31 | Rhodamine |
| Human satellite DNA | 1 | HUMSAT32 | Rhodamine |
| Human satellite DNA | 1 | HUMSAT33 | Rhodamine |

Probe Synthesis, Labeling, Hybridization, Washing and Detection

These steps are performed as in Example 1.

Results

To photograph the four fluorochromes used to label four of the differently labeled probes, four different filter cubes, having the appropriate excitation and emission filters, are used on the microscope. Photographs are then taken sequentially following the change of each filter cube.

Alternatively, dual- and triple-filter sets available from Chroma Tech, Inc., of Brattleboro, Vt.; and from Omega, Inc., of Brattleboro, Vt. may be used to allow the operator to photograph two or three different colors simultaneously (as demonstrated in Example 2 above). A color TV camera may optionally be used.

A single probe may be detected within a single cell as by the procedure used in Example 1. Two probes may be detected and viewed and photographed by the procedure used in Example 2. Three or more may be detected if reporter molecules fluorescing at differently detectable wavelengths are used. As many different probes may be differentiated as the number of different fluorescent dyes can be distinguished by the available light filter systems.

In the foregoing examples, when the fetal cell has a normal male karyotype, there is a single point of orange fluorescence (a "dot") in the nucleus of the fetal cell when the X probe is used; a single green dot when the Y probe is used; while there were two blue dots when a probe for chromosome 18 were used; two red dots when a probe for chromosome 16 is used; two orange dots when a probe for chromosome 21 is used; and 2 green dots when the probe for chromosome 13 is used, and two orange dots when a probe for chromosome 1 is used. These are the results for a male fetus with the "normal" number of chromosomes present.

Example 4

Detection of Fetal Cells by DNA Probes

A. Enrichment of Fetal Trophoblasts Circulating in Maternal Blood Using a Sorting Flow Cytometer and Fetal Cell Identification Probes Preparation of Cells Isolated white blood cells from a pregnant woman are used in the following example. The cells are washed with nuclease-free PBS and placed in a single cell suspension at a concentration that results in clearly separated cells. The cells are spun down to a pellet and the supernatant decanted. The cells are resuspended in 0.5% paraformaldehyde and left for 12–16 hours at 4° C. After fixation, the cells are spun to remove the paraformaldehyde and then washed once in PBS and resuspended in 2×SSC. The cells are used immediately.

Preparation of Probes a. Genetic Testing Probes

For a negative control probe, a 25-base sequence from the nitrogen reductase (NR) gene sequence is used (Table 6). For a positive control probe, a 25-base sequence from the 28S gene is used (Table 6).

The genetic testing probes are oligodeoxynucleotides complementary to regions of human chromosomes X, Y, 1, 13, 16, 18 and 21. The details of selection, preparation and labeling of these probes are included in Table 7 below.

b. Fetal cell identification probes.

The fetal cell identification probes (Table 8) are accessed via the Genetic Sequence Data Bank, GenBank, version 69.0 and prepared from the following gene sequences:

(1) fetal hemoglobin gene, (2) cytokeratin gene, (3) β-subunit of chorionic gonadotrophin, (4) chorionic somatomammotropin gene (human placental lactogen), (5) α-fetoprotein gene, and (6) pregnancy-specific glycoprotein genes.

The aforesaid sequences are cut into 25-mer oligodeoxynucleotides and synthesized by a DNA synthesizer as aforesaid, and in the last stage an aminohexyl phosphate linker is attached to the 5'-end of each oligonucleotide. The 5'-aminohexyl oligodeoxynucleotides are then coupled to the fluorescent dye FITC and purified by column chromatography and HPLC.

TABLE 6

Control Probes

| Probe Designation | Sequence | |
|---|---|---|
| 28S | ATCGAGTAGTGGTATTTCACCGGC | SEQ ID NO:1: |
| NR | TACGCTCGATCCAGCTATCAGCCGT | SEQ ID NO:2: |

TABLE 7

Genetic Testing Probes

| Probe Designation | Chromosome Detected | GenBank Locus Name | Fluorescent Label |
|---|---|---|---|
| Alpha-centromeric repeat | X | HUMSATAX | Rhodamine |
| Alpha-centromeric repeat | Y | HUMSATB | Rhodamine |
| Alpha-centromeric repeat | 18 | HUMREPA84 | Rhodamine |

TABLE 7-continued

Genetic Testing Probes

| Probe Designation | Chromosome Detected | GenBank Locus Name | Fluorescent Label |
|---|---|---|---|
| Collagen type IV | 13 | HUMCOL1A | Rhodamine |
| Amyloid | 21 | HUMAMYB | Rhodamine |
| Fragile X | X mut. | HUMFMR1 | Fluorescein |

The Fragile X condition, an amplification, is detected by the probe of SEQ ID NO:3:, which is further exemplified below in Example 14.

Hybridization

For the hybridization procedure using the fetal cell identification probes, to pelleted cells is added 50 μl of a hybridization cocktail consisting of 30% formamide, 5×SSC, 0.16M sodium phosphate buffer, pH 7.4, 1 μg/μl sheared DNA, 3% (v/v) Triton X-100, 5% PEG 4000, 25 mM DTT, 0.4M guanidinium isothiocyanate, 15×Ficoll/PVP, and the probe (a mixture of the fetal cell identification probes) added at a concentration of 2.5 μg/ml. Hybridizations are carried out in a humidified environment at 42° C. for 30 minutes.

TABLE 8

Fetal Cell Identification Probes

| Probe Designation | GenBank Locus Name | Fluorescent Label |
|---|---|---|
| Fetal Hemoglobin | HUMGLBN | Fluorescein |
| Human Cytokeratin | HUMCYTOK | Fluorescein |
| HCG | HUMCG3B | Fluorescein |
| HCG | HUMCG6BA | Fluorescein |
| HCG | HUMCG7B2 | Fluorescein |
| HCG | HUMCGB | Fluorescein |
| Human Somatomammotropin | HUMCS1,3 | Fluorescein |
| Alpha Fetoprotein | HUMAFP | Fluorescein |
| Pregnancy-specific β-glycoprotein | HUMGPPSB1 | Fluorescein |
| Pregnancy-specific β-glycoprotein | HUMGPPSBB | Fluorescein |
| Transferrin Receptor | HUMTFRR | Rhodamine |
| Embryonic Hemoglobin ε chain | HUMEGL1 | Cy5 |
| Embryonic Hemoglobin ζ chain | HUMHBR1 | Cy3 |

Washing

Post-hybridization, the cells are placed in a 15-ml conical tube to which is added 10 ml of Wash Solution #1. The solution is agitated until the cells are a single-cell suspension and then spun at 250×g for 5 minutes. The supernatant is removed and 10 ml of Wash Solution #2 is added to the pellet. The second wash solution is agitated until the cells are a single-cell suspension. The cells are again spun at 250×g for 5 minutes. The supernatant is removed and the cell pellet resuspended in 0.2 ml of a counterstain solution of PBS containing 0.0025% Evans Blue.

Flow Cytometer Use and Interpretation

The cells are analyzed on a Epics Elite sorting flow cytometer (Coulter Instruments). The instrument uses a 488 nm argon laser, a 525 nm band pass filter for selection of fluorescent light (FLI) and a 635 nm long pass filter for light emitted by the counterstain (FL3). For each sample analyzed, the sample containing the negative probe is analyzed first and the quad-stats are set so that less than 0.05% of the cells fall in the upper-right quadrant. Next, the sample hybridized with the positive probe is analyzed under the same parameters as the sample sorted with the negative probe. Cells that fall in the upper right quadrant are collected and are hybridized to determine fetal genetic characteristics.

Results

In this experiment, NR is used as a negative control probe while the fetal cell identification probes are the positive probes, and would identify the fetal cells that circulate in maternal blood. The fetal cells would, in turn, be "sorted" as described above then deposited onto glass slides. The fetal cells would then be analyzed with the genetic testing probes as described in Examples 1 and 2.

B. Detection of mRNA to Fetal Hemoglobin

To further illustrate and exemplify a probe population prepared for use with the present invention, the following details are provided for the first entry in Table 8. SEQ ID NO:4: is a 443-nucleotide sequence of three fragments taken from GenBank for the HUMGLBN gene. Bases 1 to 91 of SEQ ID NO:4: are from 2179 to 2269 of HUMGLBN. Bases 92 to 314 of SEQ ID NO:4: are from 2393 to 2615 of HUMGLBN. Bases 315 to 443 are from 3502 to 3630 of HUMGLBN. The population of DNA probes complementary to the target mRNA that is transcribed in the cell from SEQ ID NO:4: is prepared in accordance with the teachings herein.

More specifically, the sequences of the members of the population of probes are provided as SEQ ID NO:5: through SEQ ID NO:21:, each of which is a 25-mer oligonucleotide of DNA which is complementary to the mRNA target, which is transcribed from the genetic locus named above and more specifically exemplified as SEQ ID NO:4:. Each such probe is synthesized and labelled at 5' with FITC as described herein.

Figure 5:
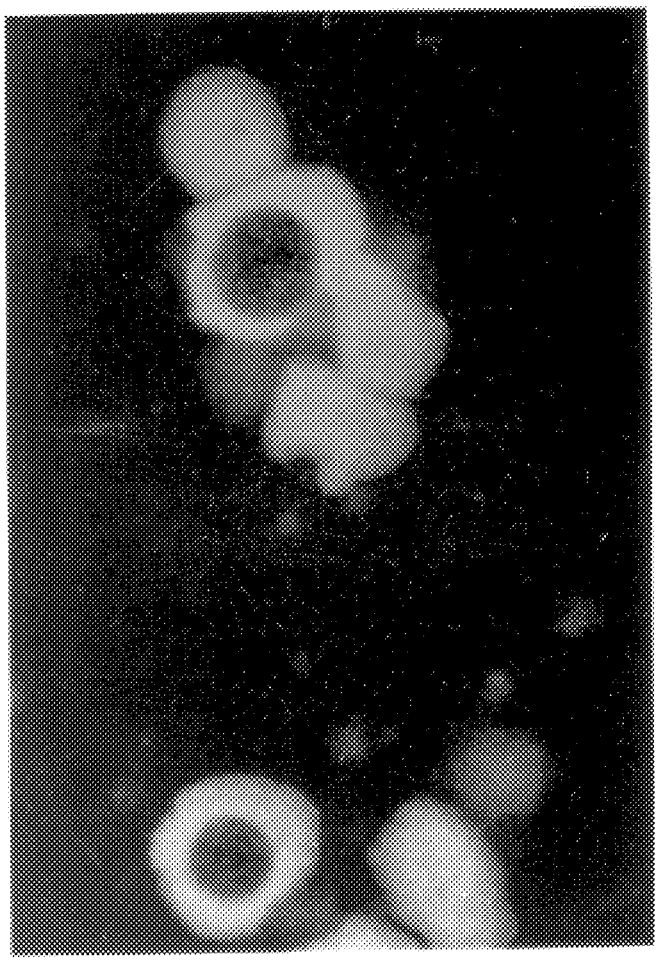
FIG. 5 shows the use of probes for fetal hemoglobin messenger RNA to identify fetal erythrocytes.

FIG. 5 is a photomicrograph showing fetal nucleated red blood cells enriched within a maternal peripheral blood sample prepared in accordance with the procedure of FIG. 3 and hybridized to the probe population described above. Cells with gray nuclei and distinctive morphology are fetal nucleated red blood cells. Cells lacking nuclei are fetal erythrocytes or fetal reticulocytes which still contain fetal hemoglobin mRNA.

C. Optional Detection of Multiple RNAs to Increase Specificity of Fetal Cell Identification As stated above, there are situations where fetal cells express two or more particular RNAs in the same cell while maternal cells from the same specimen source do not contain both RNA species in the same cell. Multiple mRNA or hnRNA species are detected simultaneously in the same cell when only the unique set of RNAs is present, so that a specific signal is detected, which uniquely identifies fetal cells.

Prior to use, cells in suspension are washed with chilled PBS and mixed thoroughly to ensure a single-cell suspension.

In the present Example, the combination of RNAs which is targeted is human chorionic gonadotropin (HCG) and transferrin receptor (TR). Although either of these genes is expressed in certain types of maternal cells, the cells which normally express these genes do not circulate in the bloodstream, and no single type of maternal cell expresses both of the genes. However, fetal trophoblasts express both of these genes simultaneously in the same cell.

One or more 25-mer oligonucleotide DNA probes for the sequences for HCG identified in Table 8 is prepared and labeled with fluorescein. One or more 25-mer oligonucleotide DNA probes for the sequence for TR identified in Table 8 is prepared, labeled with rhodamine.

A sample of maternal peripheral blood is washed with chilled PBS and mixed thoroughly to ensure a single-cell suspension placed as a smear on a microscope slide. A hybridization is performed as stated above, with probes for HCG and TR.

The signal produced in the fetal trophoblast cells is an additive combination of the green from fluorescein and the red from rhodamine, to yield a 2x signal, which appears yellow-orange.

Example 5

The Use Of Synthetic Oligonucleotides As Probes For Both Strands Of DNA As Targets For Hybridization Oligomers prepared to both strands of a DNA target produce about twice the signal when compared to the signal produced when probe is made to only one strand of the DNA. In addition, the ability to hybridize to both DNA strands allows simultaneous quantitation of the amount of DNA and RNA within individual cells.

Preparation of Cells

The H9 cell line (ATCC No. 8543) is used in the following experiment. Cultured cells are washed with nuclease-free PBS and placed in a single-cell suspension at a concentration that results in clearly separated cells. The cells are spun down to a pellet and the supernatant decanted. The cells are resuspended in 40% ethanol, 50% PBS, and 10% glacial acetic acid. The cells are used immediately.

TABLE 9

| Probe Designation | GenBank Locus Name | Fluorescent Label | Molecular Probes, Inc. Cat. # |
| --- | --- | --- | --- |
| HIV - sense strand | HUMHB102 | FITC | I-3 |
| HIV - antisense strand | HUMHB102 | rhodamine derivative | T488 |

Probe Synthesis, & Labeling

The aforementioned HIV sequences are cut into 30-base oligonucleotides and synthesized as phosphorothioate oligonucleotides using DNA synthesizers (Applied Biosystem DNA Synthesizer, Model 380B) and using the recommended A.B.I. reagents. The polysulfurized oligonucleotides are then coupled to a fluorescent dye and purified by column chromatography and HPLC. A 30-base oligonucleotide from the nitrogen reductase gene serves as the negative control probe.

Hybridization

This step is performed as in Example 4.

Washing

Post-hybridization, the cells are placed in a 15 ml conical tube to which is added 10 ml of a wash solution, consisting of 0.1×SSC, 0.4M guanidinium isothiocyanate, and 0.1% Triton X-100 (Wash Solution #1) at a temperature of 42° C. The solution is agitated until the cells are a single-cell suspension and then spun at 250×g for 5 minutes. The supernatant is removed and to the pellet is added 10 ml of Wash Solution #2 at a temperature of 42° C. The solution is agitated until the cells are a single cell suspension. The cells are spun at 250×g for 5 minutes. The supernatant is removed and the cell pellet resuspended in 0.2 ml counterstain solution consisting of 0.0025% Evans Blue in PBS.

Flow Cytometer Use and Interpretation

The cells are analyzed on a FACSTAR instrument (Becton Dickinson). The instrument uses a 5-watt argon laser coupled to a dye head, a 525 nm band pass filter for FL1 and a 584 nm band pass filter for the Rhodamine. For each sample analyzed, the sample containing the negative probe is analyzed first and the quad-stats are set so that less than 0.01% of the cells fall in the upper-right quadrant or lower-right quadrant. Next, the sample treated with the HIV probes is analyzed under the same parameters as the sample analyzed with the negative probe. Since the quad-stats are set correctly and the two samples have been handled identically, any number of cells (above 0.01%) recorded in the upper right quadrant are scored as positive for both strands and/or mRNA. Any number of cells (above 0.01%) that are recorded in the lower right quadrant are scored positive for DNA only.

Example 6

Separation of Fetal Cells from Maternal Blood and the Use of Fetal-Cell-Specific Antibodies and DNA Probes to Positively Identify the Fetal Cells Separation of Fetal Cells From Maternal Peripheral Blood Percoll stock and gradient solution was prepared in adherence to the manufacturer's (Pharmacia, Uppsala, Sweden) recommendations by mixing 9 parts of Percoll with 1 part 1.5M NaCl. The density gradient Percoll solutions were prepared according to Table 10.

TABLE 10

| Density | Percoll Stock Solution | 0.15 M NaCl | Total Volume |
| --- | --- | --- | --- |
| 1.065 | 5.15 ml | 4.85 ml | 10 ml |
| 1.075 | 6.00 ml | 4.00 ml | 10 ml |
| 1.085 | 6.83 ml | 3.17 ml | 10 ml |
| 1.100 | 8.09 ml | 1.91 ml | 10 ml |

To concentrate circulating fetal cells, 10 ml of maternal peripheral blood from a woman in the first trimester of pregnancy was overlaid in a 50 ml conical tube on a Percoll discontinuous density gradient consisting of 10 ml each of gradient solutions with densities of 1.100, 1.085, 1.075 and 1.065 g/ml from the bottom of the tube to the top, respectively. The gradient was centrifuged at 360×g for 30 minutes at room temperature. This procedure fractionated the blood in several layers. The first and second layers from the top of the gradient contained most of the circulating fetal trophoblasts. These layers were collected, diluted with PBS to a volume of 50 ml and centrifuged at 500×g for 5 minutes at room temperature. The pellet, enriched with fetal cells, was washed twice with PBS and centrifuged as above, fixed with 75% chilled ethanol and used for fetal cell identification and genetic disorder testing as described below.

As shown in FIG. 4, maternal blood cells were desirably fractionated into several bands using a four-layer Percoll discontinuous density gradient (Tube A, B). Bands 1 and 2 from the top of Tube B were withdrawn and then added to PBS (Tube C) and centrifuged for 5 minutes at 500×g. The cells were resuspended in PBS and centrifuged as above twice more. The pellet was resuspended in chilled 75% ethanol at a concentration at $10^6$ cells/ml and used the same day or stored at 20° C.

Positive Identification of Fetal Cells
  A. By Direct Immunofluorescence
  About $10^6$ ethanol-fixed maternal blood cells enriched with fetal cells were microcentrifuged at 1500 rpm for 5 minutes at room temperature. The pellet was resuspended in 1 ml of buffer A (8.01 g NaCl, 0.20 g KCl, 1.44 g $Na_2HPO_4$, 1000 ml distilled, deionized water) containing 5% fetal calf serum (buffer A/FCS) and microcentrifuged as stated above.

This wash step was repeated. The final pellet was resuspended in 100 µl of buffer A/FCS containing 1 µl of anti-human cytokeratin 18-FITC (Sigma Chemical Company Catalog No. F-4772; mouse host, IgG class 1, clone CY-90) and incubated in the dark for 1–2 hours while mixing gently on an end-to-end mixer. The reaction mixture was then washed 3 times with 1 ml buffer A/FCS as above and the pellet was cytospun on glass slides at 700 rpm for 7 minutes. Fetal cells were scored using fluorescence microscopy.

Figure 6A:
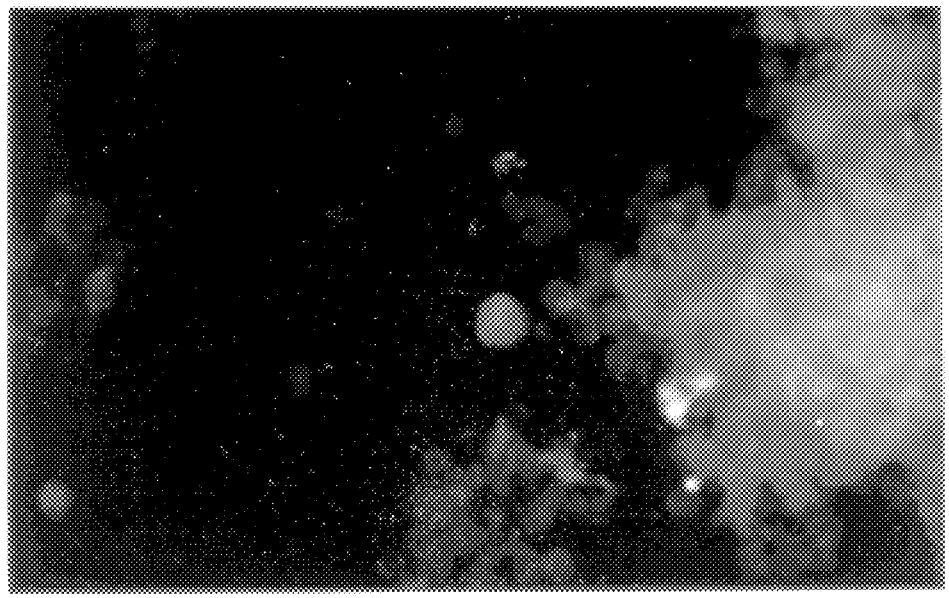
FIGS. 6A and 6B show the use of anti-cytokeratin antibodies to positively identify fetal cells in maternal blood.
Figure 6B:
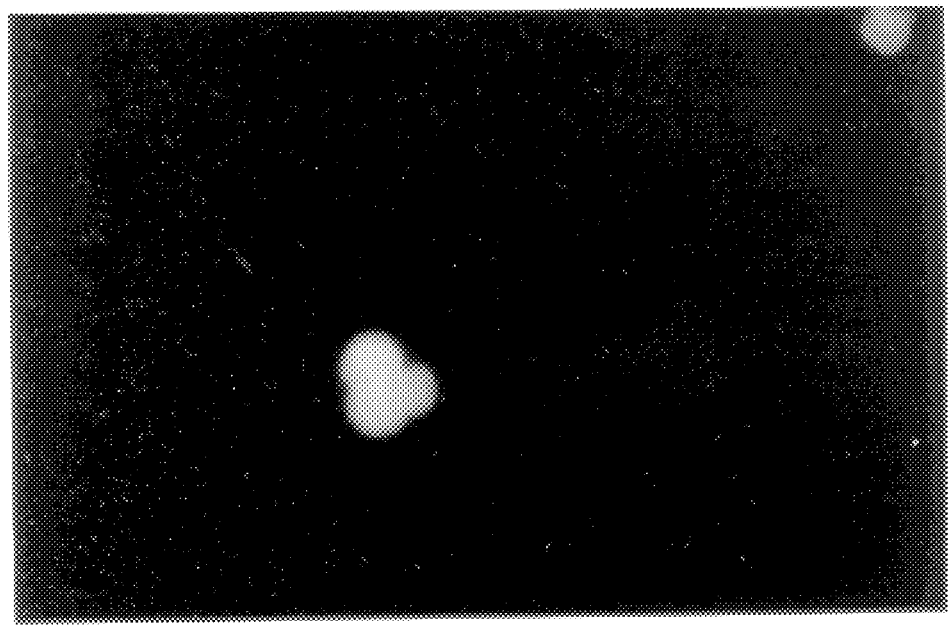

FIGS. 6A and 6B show a representation of these fetal cells stained with anti-human cytokeratin 18-FITC in maternal peripheral blood as described above.

B. By Indirect Immunofluorescence Labeling
  As an alternative to the direct immunofluorescence described above, an indirect immunofluorescence method can be used.

The procedure was the same as the direct method (described above), except the cells were first incubated in a 1:200 dilution of anti-human cytokeratin (CAM 5.2 from Becton Dickinson Catalogue No. 92-0005) in buffer A/FCS for 40 minutes and washed free of the primary antibody. The cells were then labeled with the secondary antibody tagged with FITC (anti-mouse IgG+IgM from goat); (Boehringer Mannheim Biochemicals Catalog No. 605-25) for 30 minutes and washed from the residual antibody as described above. The cells were scored as above.

C. By Sequential Use of Y Chromosome DNA Probe on Fetal Cells Previously Stained with Anti-Cytokeratin Antibody to Detect Fetal Cells and Perform Genetic Testing in Maternal Blood Preparation of Cells
  An additional slide stained with the anti-cytokeratin antibody as described above was taken through the hybridization procedure as described below.

Preparation of Probes
  The Y chromosome probes were synthetic oligodeoxynucleotides complementary to regions of human chromosome Y. The details regarding the preparation and labeling of these probes are included in Example 1 and in Table 8.

Hybridization
  For the hybridization procedure, 20 µl of a hybridization cocktail was added to the slide. The cocktail contained PEG, 25% formamide, 5×SSC, 1 mg/ml salmon sperm DNA, 15×Ficoll/PVP, 0.4M guanidinium isothiocyanate, 50 mM DTT, 5% Triton X-100, 50 mM EDTA, 50 mM $Na_2PO_4$, and the Y chromosome probe at a concentration of 20 µg/ml. A coverslip was applied and the slide was incubated at 85° C. for 15 minutes in an incubator.

Washing
  After hybridization, the slides were placed in a Coplin jar to which was added 100 ml of Wash Solution #1. The jar was agitated until the coverslip fell off, and the slide was held in this solution for 2 minutes. This wash solution was removed and Wash Solution #2 was added. This second wash solution was agitated for 1 minute and poured off, and this last wash was repeated 6 times. Following the washes, 8 µl of Mounting solution was added. The slide was coverslipped and viewed under the fluorescence microscope.

Fluorescence Detection
  Slides were screened under 40× objectives using an Olympus BH10 microscope with fluorescence capabilities.

Figure 7:
FIG. 7 shows the detection of the Y chromosome within a fetal trophoblast, positively identified using the anti-cytokeratin antibody, and isolated from maternal blood.

FIG. 7 shows a cytokeratin-stained fetal cell (brightly stained cytoplasm) within maternal peripheral blood. The cell has one Y chromosome within its nucleus that has stained positive following hybridization with the rhodamine labeled Y chromosome probe.

Example 7

Isolation of Trophoblasts from Placenta and Detection of Chromosomes X, Y and 18 Within Their Nuclei Trophoblasts were isolated from term placental tissue by a modified procedure of Wang et. al., American Journal of Reproductive Immunology 16:8–14 (1988).

The trophoblasts were then fixed with 75% chilled ethanol, stained with anti-cytokeratin antibodies as described above (Example 6) and subsequently hybridized to Y, X and 18 chromosome-specific probes also as described above in Example 6.

The origin of the probes for chromosome X, Y and 18 was described in Example 1.

The DNA probes were all labeled with a rhodamine derivative as described in Example 1.

Hybridization, washing and detection was carried out as described in Example 1.

Figure 8A:
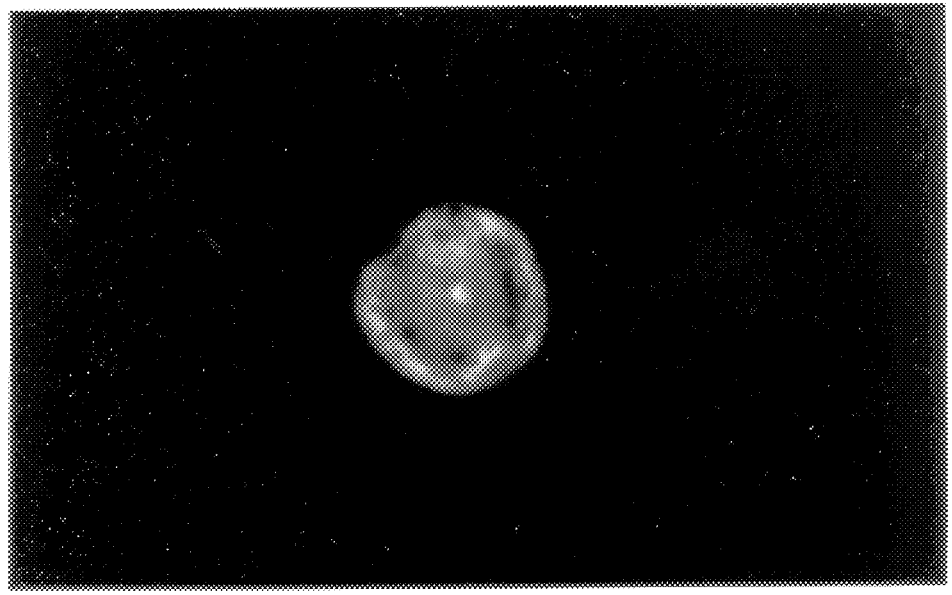
FIG. 8A shows the use of in situ hybridization to determine the numerical status of chromosomes X in placental trophoblasts that have been positively identified using the anti-cytokeratin antibody.
Figure 8B:
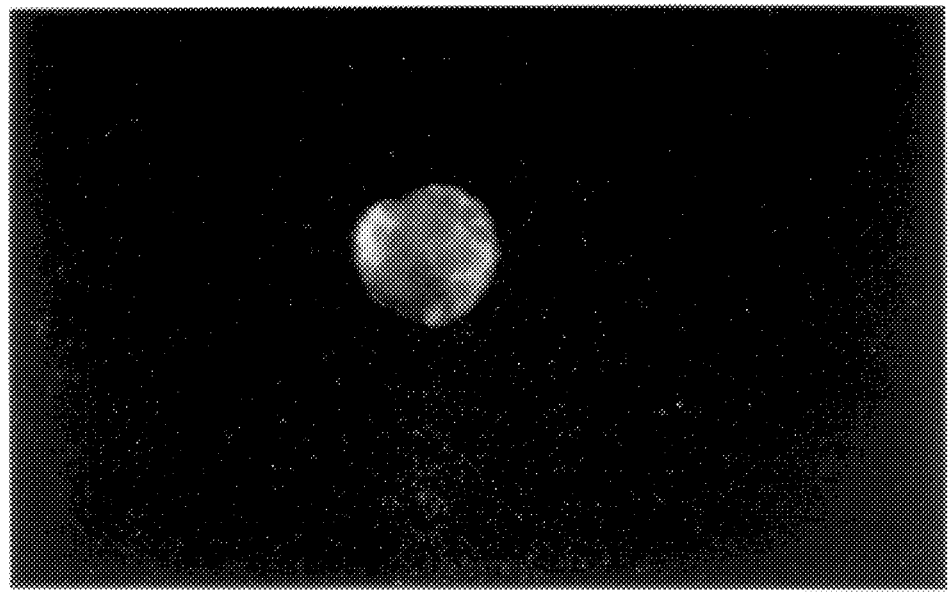
FIG. 8B shows the use of in situ hybridization to determine the numerical status of chromosomes Y in placental trophoblasts that have been positively identified using the anti-cytokeratin antibody.
Figure 8C:
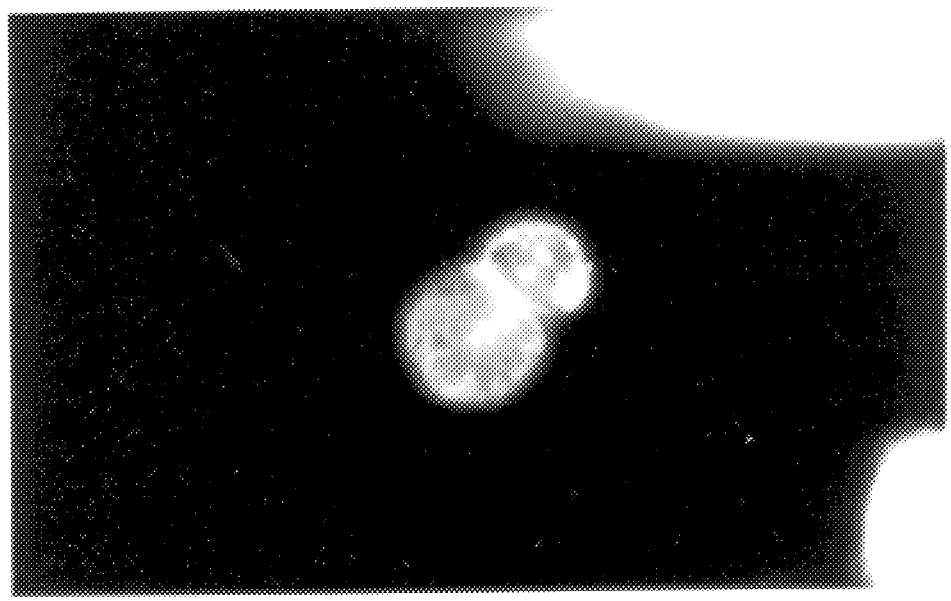
FIG. 8C shows the use of in situ hybridization to determine the numerical status of chromosomes 18 in placental trophoblasts that have been positively identified using the anti-cytokeratin antibody.

FIG. 8A shows the results with the X-chromosome probe; 8B, the Y-chromosome probe; and 8C, the chromosome-18-specific probe. The cytoplasm is stained strongly with the FITC labeled anticytokeratin antibody. The nuclei in 8A and 8B contain strong single points of light indicating the presence of single X and Y chromosomes. The nuclei in 8C contain two strong points of light indicating the presence of two chromosomes 18.

Example 8

Use of Fetal-Cell-Specific DNA Probes to Detect Fetal-Cell-Specific mRNA in Cells Obtained from Amniotic Fluid and/or Placenta Preparation of Cells Cells from amniotic fluid were prepared as described above (Example 1) and cells from placenta were prepared as described above (Example 7).

Slides containing normal peripheral mononuclear blood cells were also prepared as described in Example 2

Preparation of Probes

The fetal cell identification probes were accessed via the Genetic Sequence Data Bank, GenBank, version 69.0 and prepared from the following gene sequences, Table 11:

TABLE 11

| Probe Designation | GenBank Locus Name | Fluorescent Label |
|---|---|---|
| Human Cytokeratin | HUMCYTOK | Fluorescein or Rhodamine |
| HCG beta-subunit | HUMCG3B | Fluorescein or Rhodamine |
| Alpha Fetoprotein | HUMAFP | Fluorescein or Rhodamine |

The aforementioned sequences were cut into several 39-base-oligonucleotides and synthesized as phosphorothioate oligonucleotides using DNA synthesizers (Applied Biosystems DNA Synthesizer, Model 380B) and using the recommended A.B.I. reagents. The polysulfurized oligonucleotides were then coupled to a FITC (Molecular Probes, Inc. Catalogue No. I-2) or rhodamine (Catalogue No. T488) and purified by column chromatography and HPLC. As a negative control probe, the HIV probes described in Example 10 were used.

Hybridization

For the hybridization procedure, 20 µl of a hybridization cocktail was added to each slide. The cocktail consisted of 31% PEG, 25% formamide, 5×SSC, 1 mg/ml salmon sperm DNA, 15×Ficoll/PVP, 0.4M guanidinium isothiocyanate, 50 mM DTT, 5% Triton X-100, 50 mM EDTA, 50 mM $Na_2PO_4$, and probe at a concentration of 20 µg/ml. A coverslip was applied to each slide and was incubated for 30 minutes at 42° C.

Washing

This step is performed as in Example 6.

Fluorescence Detection

Photomicrographs were taken on an Olympus BH10 microscope with fluorescence capabilities, using Kodak Ektachrome EES-135 (PS 800/1600) film, exposed, and push processed at 1600 ASA. A 20-second exposure time was consistently used, so that direct comparisons could be made between all photomicrographs taken.

In each of the cells in the figures below, the bright light (in color photographs, it is orange) from both the nuclei and cytoplasm represent a positive signal. The unstained cells in the photos (in color photographs, it is a red color due to the counterstain) represent maternal cells that are negative for the presence of the fetal cell identification probes.

As a negative control, the HIV probes were hybridized to these amniocytes and trophoblasts and there was no bright hybridization signal.

All of the fetal cell identification probes as well as the HIV probes were used in separate hybridization experiments using normal white blood cells and these cells had no bright hybridization signal indicating that they were all appropriately negative.

Figures 1, 9A:
Figures 2, 9A:
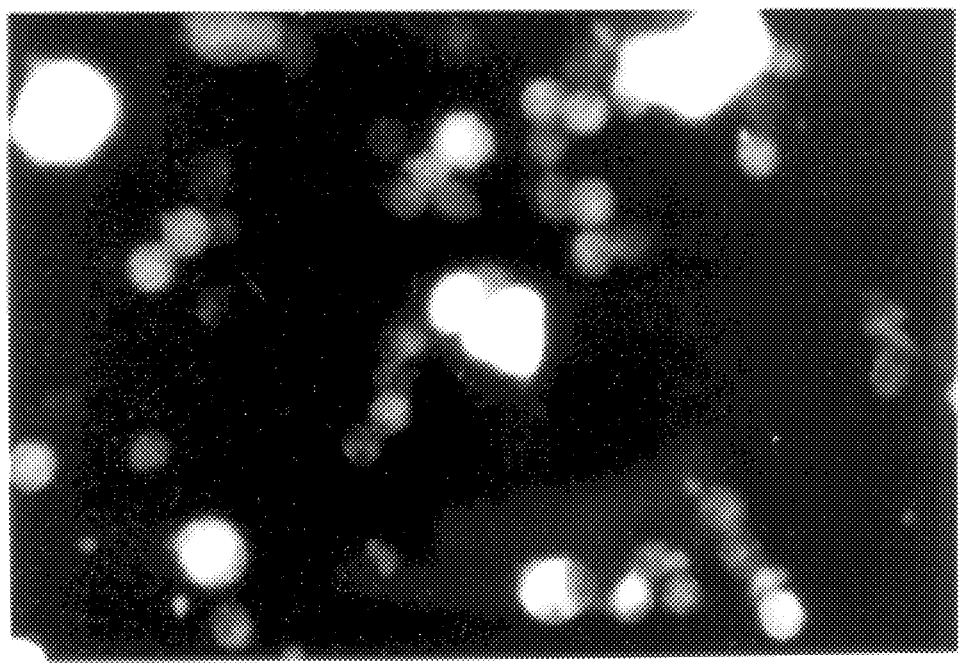

FIG. 9A shows the results when using the cytokeratin probes to analyze amniocytes (top panel) and trophoblasts (bottom panel).

Figures 1, 9B:
Figures 2, 9B:
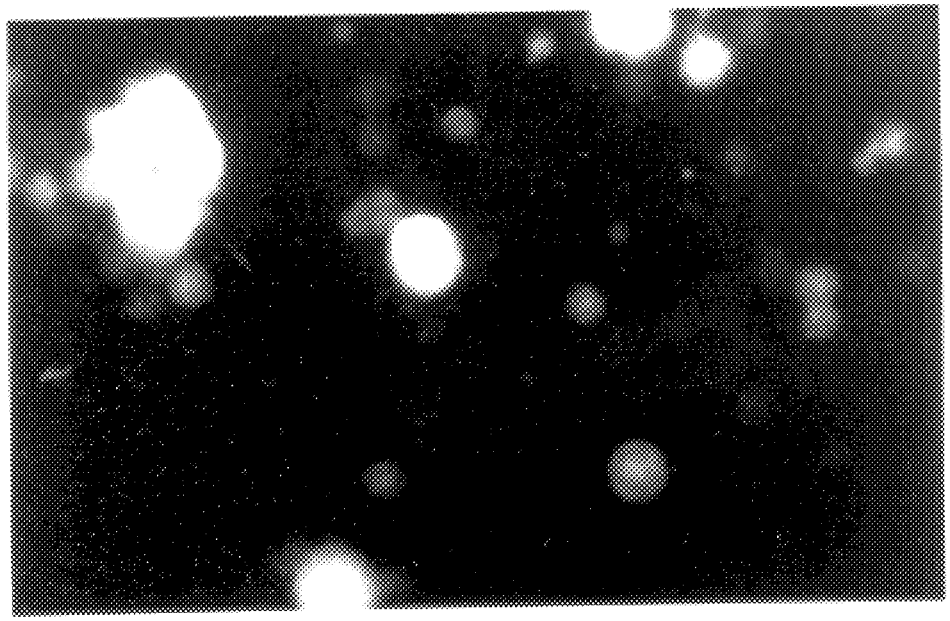

FIG. 9B shows the results when using the HCG probes to analyze amniocytes (top panel) and trophoblasts (bottom panel).

Figures 1, 9C:
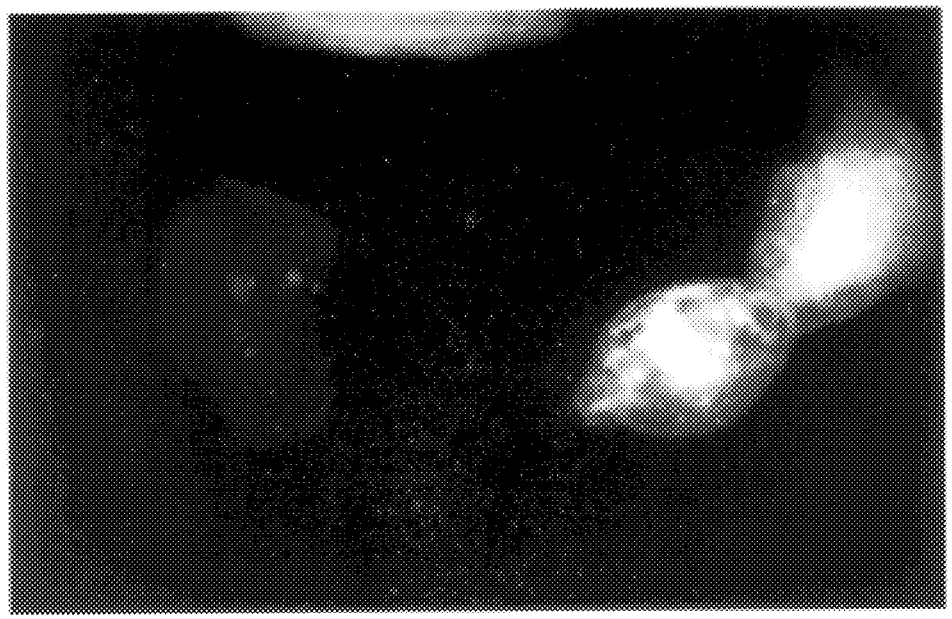
Figures 2, 9C:
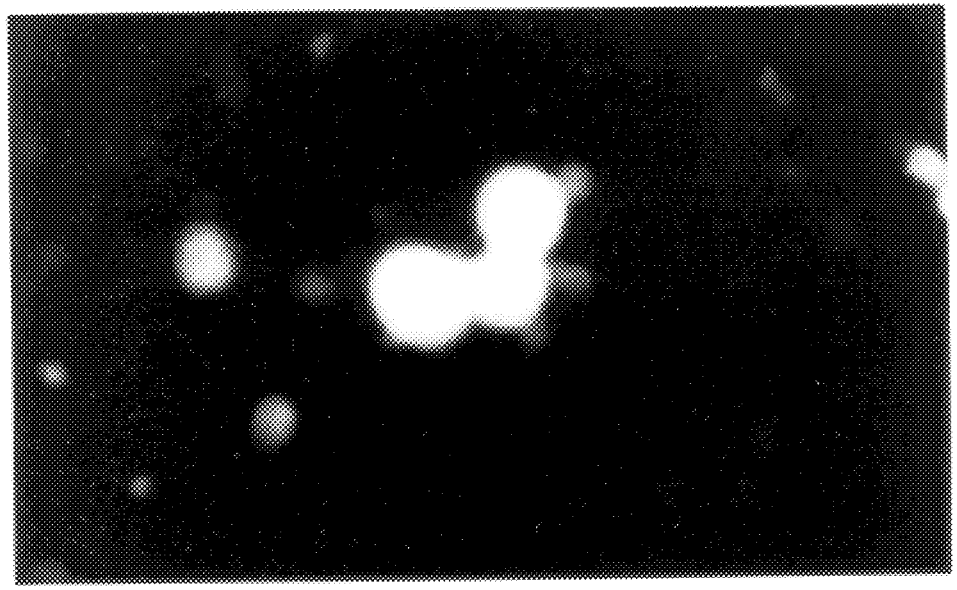

FIG. 9C shows the results when using the α-fetoprotein probes to analyze amniocytes (top panel) and trophoblasts (bottom panel).

Example 9

Use of Anti-Cytokeratin Antibodies and Flow Cytometry to Detect Fetal Trophoblasts Obtained from Placental Tissue Preparation of Cells Placental trophoblasts were isolated from term placenta and were fixed in 75% chilled ethanol as described in Example 2. The fixed cells were stained with anti-cytokeratin and isotope-control antibodies, both labeled with FITC as stated in Example 6 and analyzed by flow cytometry.

Flow Cytometer Use and Interpretation

The cells were analyzed on a Profile II system (Coulter Instruments). The instrument uses a 488 nm argon laser, a 525 nm band pass filter for FL1. For each sample tested, the sample containing the isotope control antibody was analyzed first and the controls of the instrument (quad-stats) set so that less than 0.2% of the cells fell in the upper-right quadrant. Next, the sample challenged with the anti-cytokeratin antibody was analyzed under the same parameters as the sample challenged with the isotope-control antibody. Since the quad-stats had been set correctly and the two samples had been handled identically, the amount of cells above 0.2% that were recorded in the upper right quadrant were scored as positive.

Example 10

Use of HIV DNA Probes to Detect HIV mRNA in Placental Fetal Trophoblasts or Amniocytes Preparation of Cells Trophoblasts are isolated from term placental tissue by a modified procedure as described in Example 7. Amniocytes are obtained through amniocentesis. The H9 HIV cell line and peripheral blood polymorphonuclear cells served as positive and negative controls, respectively. These cells are washed with nuclease-free PBS and are placed in a single-cell suspension at a concentration resulting in clearly separated cells. The cells are spun down to a pellet and the supernatant decanted. The cells are resuspended in 0.5% paraformaldehyde and left for 12–16 hours at 4° C. After fixation, the cells are spun to remove the fixative and then washed once in PBS and resuspended in 2×SSC. The cells are used immediately.

Preparation of Probes

A negative control probe, sequences for human papillomavirus (HPV) type 16 and HPV type 18 (Table 12) were obtained from the published sequences and were accessed via the Genetic Sequence Data Bank, GenBank, version 69.0.

TABLE 12

| Probe Designation | GenBank Locus Name | Fluorescent Label |
|---|---|---|
| HPV 16 | PPH16 | Fluorescein |
| HPV 18 | PPH18 | Fluorescein |
| HIV | HUMBH102 | Fluorescein |

Twenty separate HPV probes (10 for HPV type 16 and 10 for type HPV 18) and 180 HIV probes are synthesized by cutting the HIV sequences into several 39-base oligonucleotides and synthesized as phosphorothioate oligonucleotides using DNA synthesizers (Applied Biosystems DNA Synthesizer, Model 380B) and using the recommended A.B.I. reagents. The phosphorothioate oligonucleotides are then coupled to FITC and purified by column chromatography and HPLC.

Hybridization

For the hybridization procedure, to pelleted cells was added 50 µl of an hybridization cocktail consisting of 30% formamide, 5×SSC, 0.16M sodium phosphate buffer, pH 7.0, 1 µg/ul sheared DNA, 3% (v/v) Triton X-100, 5% PEG 4000, 25 mM DTT, 0.4M guanidinium isothiocyanate, 15×Ficoll/PVP, and the probe added at a concentration of 2.5 µg/ml. Hybridizations were carried out in a humidified environment at 42° C. for 30 minutes.

Washing

Post-hybridization, the cells were placed in a 15 ml conical tube to which was added 10 ml of Wash Solution #1 (heated to 42° C.). The solution was agitated until the cells were a single-cell suspension and then spun at 250×g for 5 minutes. The supernatant was removed and to the pellet was added 10 ml of Wash Solution #2 (heated to 42° C.). The second wash solution was agitated until the cells were a single-cell suspension. The cells were spun at 250×g for 5 minutes. The supernatant was removed and the cell pellet resuspended in 0.2 ml of a PBS counterstain solution containing 0.0025% Evans Blue.

Flow Cytometer Use and Interpretation

The cells were analyzed on a Profile II system as aforesaid. The instrument uses a 488 nm argon laser, a 525 nm band pass filter for FL1 and a 635 nm band pass filter for FL3. For each sample analyzed, the sample containing the negative probe was analyzed first and the quad-stats set so that less than 0.01% of the cells fell in the upper-right quadrant. Next, the sample analyzed with the positive probe was analyzed under the exact same parameters as the sample analyzed with the negative probe. Since the quad-stats had been set correctly and the two samples had been handled identically, cells (above 0.01%) recorded in the upper right quadrant were scored as positive.

Example 11

Synthesis of Multiple-Reporter Labeled Oligonucleotides

To obtain maximum sensitivity, a preferred embodiment of the present invention employs oligonucleotide probes that are labeled with multiple reporter moieties, such as fluorescent moieties. This Example describes the preparation of such probes.

Two hundred µg of dried oligonucleotide is dissolved in 100 µl of 250 mM Tris buffer pH 7.4, to form a first solution. One mg of iodoacetamido-fluorescein is combined with 100 µl of dry DMF to create a 200-µl reaction mixture. The two solutions are mixed together and shaken overnight. This results in an oligonucleotide to acetamido-fluorescein ratio of 1:5 in the reaction mixture. One mg of iodoacetamido-fluorescein is again combined with 100 µl of DMF, and this 100 µl is combined with the 200 µl of reaction mixture. Another 100 µl of 250 mM Tris buffer is added to the 400 µl of reaction mixture and the reaction is allowed to continue for another 6 hours. The labeled oligonucleotide is precipitated with ethanol and 3M sodium acetate. This crude material is then loaded on to a PD-10 column to remove free dye. The desired fractions are collected. The liquid phase is then removed under vacuum. The crude material is then purified by high performance liquid chromatography (HPLC).

Example 12

Probes for Both Strands of a DNA Target

The procedure of the Examples above may be modified as follows:

(1) Four hundred sixteen (416) separate probes (208 for type 16 and 208 for type 18) each designed as 30-bases in length, are synthesized. However, in addition to making probes corresponding to those 416 separate oligonucleotides that together comprise probes for one strand of each of the two HPV targets, 416 additional oligonucleotide probes were made for the second strand of each of the two HPV targets. The probes for the first strand are made staggered relative to the second strand probes as regards how they map on a map of the HPV genome. As a result, one-half (15 nucleotides) of each first strand probe will be complementary (in nucleotide sequence) to one-half of one second strand probe and the other half (15 nucleotides) of that first strand probe will be complementary to a portion of another second strand probe. Staggering of the probes means that, because of the shortness of the overlap (15 nucleotides), probes of the first strand will not hybridize significantly to probes of the second strand. On the other hand, about twice as much hybridization is detected as compared to the situation where only probes corresponding to one strand are used.

(2) Probes are made as phosphorothioate oligonucleotides, each 30-mer having four sulfur atoms, using an Applied Biosystem (ABI) DNA Synthesizer, Model 380B and the recommended A.B.I. reagents. The sulfur atoms are located as follows: one is at the extreme 5' end of the probe, a second is between the 7th and 8th nucleosides (counting from the 5' end), the third is between the 22nd and 23rd nucleosides, and the fourth is between the 29th and 30th nucleosides. The sulfur atoms of the polysulfurized oligonucleotides are then coupled to a fluorescent dye, iodoacetamido-fluorescein, as follows (smaller amounts can be synthesized by adjusting the volumes): 200 µg of dried oligonucleotide is dissolved in 100 µl of 250 mM Tris buffer, pH 7.4 to form a first solution. Then 1 mg of iodoacetamido-fluorescein is combined with 100 µl of dry dimethylformamide (i.e., 100 percent DMF) in a second solution. The two solutions are mixed together and shaken overnight. After the overnight incubation, the labeled oligonucleotide is precipitated with ethanol and 3M sodium acetate. This crude material is then loaded on to a PD-10 column to remove free dye. The desired fractions are then collected. The liquid phase is then removed under vacuum. The crude material is then purified with HPLC (high performance liquid chromatography).

(3) Negative control probes are constructed in analogy to steps (1) and (2).

(4) The hybridization cocktail is modified as follows: 1.5% PEG is used instead of 31% PEG, 30% formamide is used instead of 21% formamide, 10% DMSO (10% v/v) is included, and 5% (v/v) of vitamin E is included. Also instead of adding 50 µl of the hybridization cocktail to the slide, 40 µl of the cocktail is added to 5 µl of squalene plus 5 µl of pyrrolidinone and the combined 50 µl is added to the slide. It can be useful to add 5 µl of 1M (1 molar) DTT and 5 µl of Proteinase K (1 mg/ml) solution per 100 µl of hybridization cocktail and run the hybridization reaction at, for example, 42° C. for 5 minutes, then at 95° C. for 5 minutes, and then at 42° C. for 2 minutes. It can also be useful to add about 0.05% or 0.10% aurintricarboxylic acid (ATA) in the hybridization cocktail.

(5) Instead of adding 8 µl of antifade/Hoechst to the slide, 8 µl of the following solution is added: 9 volumes of solution A plus 1 volume of solution B where solution A is 0.01% 1,4 diphenylamine (antifade) plus nuclear stain Hoechst (#33258; 1 µg/ml) plus 0.0025% Evans Blue in 50% (v/v) glycerol plus 50% (v/v) 1×PBS (0.136M NaCl, 0.003M KCl, 0.008M $Na_2HPO_4$, 0.001M $KH_2PO_4$) and solution B is dodecyl alcohol.

Example 13

The Use of DNA Probes and In Situ Hybridization to Determine the Presence of the Philadelphia Chromosome Preparation of Cells White blood cells from peripheral blood or bone marrow from patients with chronic myelogenous leukemia are deposited onto glass slide by the cytospin method.

Preparation of Probes

Several 25-base synthetic oligonucleotide probes are prepared from the DNA sequence listed in the table below.

TABLE 13

| Probe Designation | Chromosome Detected | GenBank LocusName |
| --- | --- | --- |
| BCR | 22 | HUMBCR |

Probe Synthesis and Labeling

The oligodeoxynucleotides are synthesized and labeled as described in Example 1.

Hybridization For the hybridization procedure, the cells are deposited onto slides. 20 to 25 µl of a hybridization cocktail consisting of 31% PEG, 30% formamide, 5×SSC, 0.1M sodium phosphate buffer, pH 7.4, 100 µg/ml low molecular weight, denatured, salmon or herring sperm DNA, 10% (v/v) Triton X-100, 10% DMSO, 15×Ficoll/PVP, 0.4M guanidinium isothiocyanate, 10 mM DTT, and 0.025M EDTA and the probe added at a concentration of 20 µg/ml is applied.

A coverslip is applied and the slide is heated to 95° C. for 5 minutes, allowed to cool to 42° C. and incubated for 25 minutes at that temperature.

Washing and Detection

Washing and detection are done as described in Example 1.

Chronic myelogenous leukemia is associated with a characteristic chromosomal translocation between chromosomes 9 and 22, resulting in the so-called Philadelphia Chromosome, 22q+. [See: Rowley, J. D.: A new consistent chromosomal abnormality in myelogenous leukemia identified by quinacrine fluorescence and Giemsa staining. Nature 243:290 (1973); Heisterkamp N, et al.: Structural organization of the bcr gene and its role in the Ph translocation. Nature 315:758 (1985)]

Because the probes for the bcr gene are prepared such that they span the break point cluster region to include both the 5' and the 3' ends of the gene, when a translocation occurs there are three points of light ("dots") within the cell. One bright dot would represent the unaffected chromosome and two less intense dots would represent the un-translocated 5' bcr gene while the second less intense dot would represent that 3' end of the bcr gene that translocated to Chromosome 9.

In an alternative format, sequences from the c-abl gene that translocate to Chromosome 22 are accessed and prepared as described above. These sequences are labeled with a second fluorescent moiety and added to the hybridization solution. Now when a translocation occurs, one positive signal (representing the 5' end of the bcr gene still on Chromosome 22) would appear in one color (e.g., green) and adjacent to another positive signal (representing the c-abl gene that translocated to Chromosome 22) which would appear in a second color (e.g., red).

Example 14

Detection of the Fragile X Chromosome in Amniocytes and in Peripheral Blood Mononuclear Cells Preparation of Cells Two ml of Amniotic fluid is diluted to 10 ml with PBS and centrifuged at 1200 rpm for 10 minutes. The resultant cell. pellet is suspended in 800 pl of ethanol and methanol (v:v, 3:1). 200 µl of the sample is deposited on each slide by the cytospin method. In addition, approximately 5,000 peripheral blood mononuclear cells obtained from a normal male are deposited onto a glass slide by the cytospin method.

Preparation of Probes

A 25-base synthetic oligonucleotide consisting of SEQ ID NO:3: is synthesized and labeled as described in Example 1.

Hybridization, Washing and Detection

Hybridization, washing and detection are done as described in Examples 1 and 13.

The Fragile X syndrome is caused by mutations that increase the size of a specific DNA fragment (containing a lengthy CGG repeat) of the X chromosome (in Xq27.3). See, e.g., Francois Rousseau, M. D. et al., N Engl J Med, 325:1673–1681 (1991).

Following the aforesaid procedure, when an amplification of the CGG DNA fragment is present, there is an increase in the intensity of the signal. Using any of a number of image analysis systems, this signal is quantified and compared to normal controls to determine whether or not a Fragile X chromosome, i.e., an amplification of CGG, is present. Such image analysis systems include, for example: ACAS 570 from Meridian Instruments, Okemos, Mich.; and instruments from Perseptive Systems, Inc., League City, Tex.; and Applied Imaging, Santa Clara, Calif.

Example 15

Concentration of Fetal Nucleated Red Blood Cells Within Maternal Blood Using Direct Negative Selection Method A sample consisting of 20 ml of maternal peripheral blood is diluted to 35 ml with buffer solution A and overlaid on top of 15 ml Histopaque-1083 in a 50-ml conical tube. The tube is centrifuged at 700×g for 30 minutes, and the interphase layer is collected into a fresh 50-ml conical tube, the volume then being brought up to 40 ml with buffer A. The conical tube is then centrifuged for 10 minutes at 1000 rpm (200×g). The cell pellet is re-suspended in 1 ml of buffer solution B and mixed with pre-washed immunomagnetic beads coated with anti-CD45. The bead/cell mixture is allowed to react for 10 minutes, during which the unwanted leucocytes are reacted to the beads while nucleated red blood cells (NRBCs) stay in the solution. A magnetic particle concentrator is applied to the side of the reaction tube. The magnetic beads and material complexed thereto collect on the side of the reaction tube adjacent the magnet. The supernatant fluid, containing NRBCs, is then poured off, cytospun, fixed for 5 minutes in 80% ethanol and used for in situ hybridization.

Example 16

Concentration of Fetal Nucleated Red Blood Cells Within Maternal Blood Using Alternate Direct Negative Selection Method The procedure of Example 15 is performed, but with the following modification: Instead of using immunomagnetic beads coated with anti-CD45, a cocktail containing immunomagnetic beads coated with monoclonal antibodies against various components of maternal blood (but not fetal erythrocytes) is used to effectively remove the non-fetal cells as well as platelets from the specimen, leaving behind the fetal target cells.

Antibody Selection

To determine whether a particular antibody or mixture of antibodies would be suitable for use in accordance with the present invention, the following procedure may be performed:

Perform a density separation on a sample of umbilical cord blood as in Example 4. Resuspend the buffy-coat in 1 ml of Buffer Solution B. Prepare a control slide by cytospinning 50 µl of this cell suspension and fixing by dipping slide in 3:1 ethanol/methanol. Prepare a test slide by removing a sample of 1×10$^6$ cells from the aforesaid buffy-coat resuspension and adding 20 µg of the antibody to be tested, coupled to magnetic beads. Prepare the cells as described in Example 6. Perform microscopic examination of slides as in Example 6 and determine the ratio of fetal nucleated red blood cells to total cells on each slide. If the ratio for the test slide is between 75% and 125% of the corresponding ratio for the control slide, the antibody is considered acceptable. For example, an acceptable result would be a control slide having 5 NRBCs per 10,000 cells and the corresponding test slide having 4 NRBCs per 10,000 cells.

Example 17

Concentration of Fetal Nucleated Red Blood Cells Within Maternal Blood Using Indirect Negative Selection Method A 20-ml sample of maternal peripheral blood is diluted to 36 ml with buffer solution A and overlaid on the top of 15 ml of Histopaque 1083 in a 50-ml conical tube. The tube is centrifuged at 700×g for 30 minutes, and the interphase layer (buffy-coat) is collected into a fresh conical tube. The volume is then brought up to 40 ml with buffer solution A and the tube is centrifuged for 10 minutes at 200 ×g. The cell pellet is re-suspended in a solution containing monoclonal antibody. The monoclonal antibody is anti-CD45 or a mixture of monoclonal antibodies selected from the group consisting of anti-CD45, anti-CD34, anti-CD12, anti-CD31, and anti-CD44 in a 1-ml reaction volume. The cells are allowed to react with the antibody for 30 minutes at 4° C. The mixture is then transferred to a microcentrifuge tube and centrifuged at 500 rpm for 5 minutes, and the supernatant is aspirated off. The cell pellet is washed with 1400 µl of the reaction buffer (buffer solution A), and the pellet is re-suspended in 1 ml buffer solution B. The cell suspension is then mixed with pre-washed bends coated with sheep anti-mouse IgG, and the mixture is allowed to react for 10 minutes during which most of the non-wanted cells (leucocytes and erthyrocytes) react with the beads, forming cell/bead complexes. The complexes are then removed from the reaction by a magnetic particle concentrator, which collects the complexes on the side of the reaction tube. The supernatant containing NRBCs is directly loaded on cytospin to make slides. The slides are fixed with 80% ethanol and used for fluorescent in situ hybridization.

Example 18

Detection of Fetal Nucleated Red Blood Cells Enriched from Maternal Blood and Simultaneous Detection of Chromosome Abnormalities Slides prepared in accordance with Examples 15, 16 and 17 are hybridized on slides in a single step using probes for fetal hemoglobin mRNA as in Example 3 and probes for human chromosomes as in Example 4.

Figure 10:
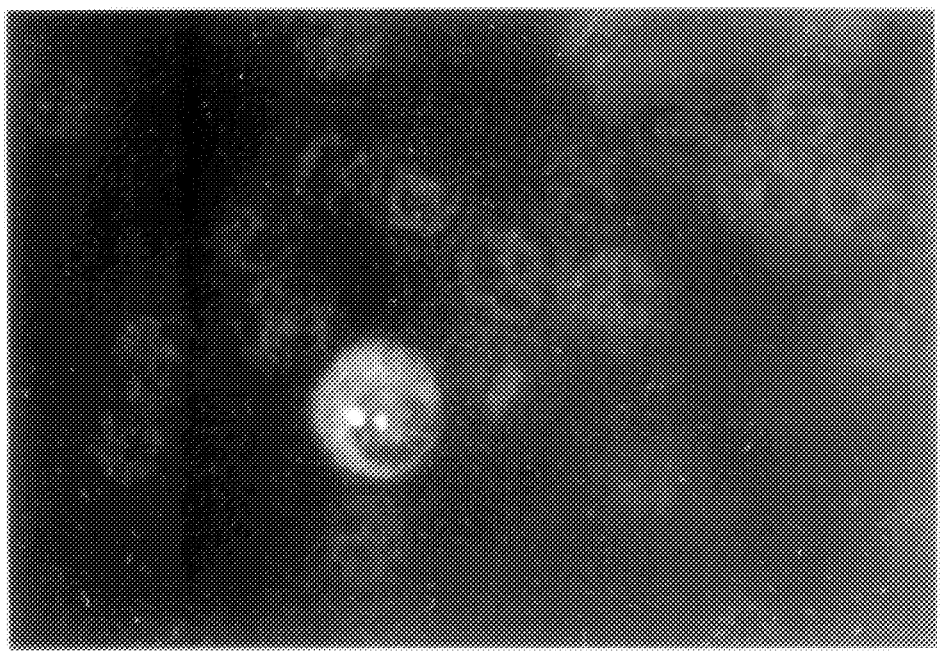
FIG. 10 shows the use of in situ hybridization to fetal-cell-specific mRNA and to chromosomes X and Y in fetal erythrocytes.

FIG. 10 shows a fetal nucleated red blood cell that was hybridized simultaneously to DNA probe s specific to fetal hemoglobin mRNA as described in Example 4, part B and to probes for human chromosomes X and Y as described in Example 4, part A. The greenish cytoplasm indicates that the cell is a fetal nucleated red blood cell , due t o signal from fluorescein-labeled probe for HbF mRNA. The green dot within the nucleus is a signal for X chromosome , from fluorescein-labeled probes for X.

The red dot within the nucleus is a signal for Y chromosome, from rhodamine-labeled probes for Y.

Example 19

Detection of Fetal Nucleated Red Blood Cells Enriched From Maternal Blood Using Indirect Immunofluorescence Techniques An alternative procedure for detecting fetal cells is to perform the procedure of Example 18, modified as follows: Instead of using DNA probes to fetal hemoglobin mRNA, monoclonal antibody against fetal hemoglobin protein (Accurate Chemical, cat. no. IRXG-11149) is used. Enriched cells are fixed in 2% paraformaldehyde for two hours, washed free of fixative and reacted with a 1:100 dilution of anti-HbF antibody for 30 min. The amount of antibody added is 2–20 µg per million fetal erythrocyte cells in the sample. The excess antibody is removed by washing the cells twice with PBS. Next the cells are stained for 30 min. with a 1:100 dilution of a monoclonal antibody that selectively binds to th e anti-HbF antibody (Euro-Path, Ltd.) and that is tagged with alkaline phosphatase. Excess antibody is removed by washing with PBS, and Vector Red as a substrate (Vector Chemical Co.) is added to the cells. In a later step, excess substrate is washed off. The cells are cytospun on glass slides and used for in situ hybridization, as in Example 18.

Example 20

Enrichment of Fetal Cells Within Maternal Blood By Lysing Maternal Erythrocytes

Maternal blood specimens are treated with 0.075M KCl for 15 min at 37° C. This treatment selectively lyses maternal erythrocytes, leaving intact all nucleated cells present in the sample. The lysate is then contacted with beads coated with anti-CD45 or, more generally, with one or more antibodies against cell surface antigens of maternal blood cells. The mixture is allowed to react. The beads along with cells bound thereto are then removed from the mixture with a magnetic particle collector. The remaining liquid, containing primarily fetal nucleated erythrocytes, is used to make cytospun slides as described hereinabove. This procedure may be performed entirely in an automated device.

Example 21

In Situ Amplification for Fetal Cell Detection

Fetal cells contain unique mRNAs, or mRNA species which are produced in cell types which do not normally contain the particular mRNA species. The detection of these RNAs, whether detected as messenger RNAs (mRNAs) or heteronuclear RNAs (hnRAs) can serve to identify cells, or even subcellular fractions as fetal or embryonic in origin. While certain RNA populations are present in high abundance (e.g., fetal hemoglobin in fetal nucleated red blood cells), other fetal- or embryonic-specific RNAs are present in low abundance, either alone or even when considered as a population of fetal-specific RNAs. The ability to detect rare mRNAs or hnRNA and thereby identify fetal cells may be enhanced by amplifying the rare RNA population using one of the available amplification techniques such as 3SR, LCR, Q-Beta Replicase, Strand Displacement Assay, PCR, and the like.

In the present invention, cells may be obtained from umbilical cord blood, maternal peripheral blood, amniotic fluid, chorionic villus samples, etc. Cellular samples may be used directly or may be concentrated to enrich the population of fetal cells prior to analysis. Cells may be fixed in common precipitating fixatives or cross-linking fixatives or may be used in the following test without fixation. The procedure may be carried out with cells deposited onto a solid support such as a glass microscope slide or used with the cells in suspension. Prior to use, cells in suspension may be washed with chilled phosphate-buffered saline (PBS), and mixed thoroughly to insure a single-cell suspension.

For in situ cDNA synthesis of the DNA copy of the rare RNA species, a "first strand mix" is freshly prepared, comprising 5 $\mu$l of 10 × first strand buffer (1.4M KCl, 0.5M Tris-HCl pH 8.1 at 42° C., 80 mM $MgCl_2$), 5 $\mu$l dithiothreitol (DTT), 5 $\mu$l 5 mM deoxynucleoside triphosphates (dNTPs), 25 pmol of each forward primer, 80 units RNase inhibitor (RNasin, Promega Corporation, Madison, Wis.) and water to a total volume of 28 $\mu$l. The dNTPs comprise an equimolar mixture of deoxynucleotide triphosphates of A, T, G and C. The cells are heated to 65° C. for 3 minutes then cooled on ice. The "first strand mix" is added, followed by 40 units of reverse transcriptase (Super RT AMV Reverse Transcriptase, HT Biotechnology Ltd., Cambridge, United Kingdom). The cells and reagents are mixed and incubated at 42° C. for 1 hour, then, for cells in suspension, the cells are spun down, washed in 200 $\mu$l PBS (pH 7.2) containing 0.1M glycine (PBS/0.1M glycine) and resuspended in 20 $\mu$l of the same buffer for use immediately in PCR; for cells on slides, the slides are washed in PBS (pH 7.2) containing 0.1M glycine (PBS/0.1M glycine) and left in the same buffer for use immediately in PCR. Primers either consist of RNA-specific primers or random primers and oligothymidine (dT).

Reactions are conducted either directly on glass microscope slides or in 50-$\mu$l volumes in 0.5 ml Sarstedt tubes containing 10 $\mu$l of the fixed template cells in PBS/0.1M glycine buffer, 25 pmol back primer, 25 pmol forward primer, 200 $\mu$M dNTPs, 5 $\mu$l 10 ×Taq polymerase buffer (Promega Corporation, Madison Wis.) and 2.5 units of Taq polymerase. The slides/tubes are subjected to 10 to 40 cycles of PCR with denaturation at 95° C. and extension at 72° C. for 1 minute each. Annealing is for 1 minute at temperatures ranging from 60° C. to 72° C. A terminal cycling oven (M.J. Research, Watertown Mass.) is used for the cells in solution and an inverted heat block on a standard thermal cycler (Perkin Elmer, Norwalk, Conn.) is used for the slides, with the slides coverslipped with mineral oil sealing the edges of the coverslip.

Following PCR amplification, cells are spun down, washed in 200 $\mu$l PBS (pH 7.2) containing 0.1M glycine (PBS/0.1M glycine) and resuspended in 20 $\mu$l of the same buffer for use immediately with in situ hybridization analysis; for cells on slides, the slides are washed in PBS (pH 7.2) containing 0.1M glycine (PBS/0.1M glycine) and left in the same buffer for use immediately with in situ hybridization analysis.

Cells which contain fetal-specific RNAs are either detected directly when using fluorescently labeled primers, are detected through a second-step detection process when primers are used which are labeled with biotin or digoxigenin, or are detected after hybridization to the amplified material, for example using the in situ hybridization system of U.S. Pat. No. 5,225,326.

Example 22

Use of Anti-CD45 Antibodies and Flow Cytometry to Detect HbF mRNA and X and Y Chromosomes Preparation of Cells Twenty milliliters (20 ml) of peripheral blood from pregnant women of 10-20 weeks gestational age are collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system. The IHbF system protocol is disclosed below.

Separation of Fetal Cells from Maternal and Cord Blood

Twenty microliters (20 $\mu$l) of the cord sample is added to the 20 ml of the maternal sample. Ten milliliters (10 ml) of the sample is thoroughly mixed and diluted to thirty milliliters (30 ml) with 2 volumes of Cell Buffer A (CBA). The diluted sample is then layered on a density gradient material, at room temperature, consisting of 15 ml Histopaque-1107 (Ten Milliliters (10 ml) Histopaque-1119 plus Five Milliliters (5 ml) Histopaque 1083) which has a density of 1.086 g/ml. Centrifugation for thirty 30 minutes at 700×g (1900 rpm) at 22° C. without brake and separation are carried out according to the manufacturer's instructions. The buffy-coat of cells is then collected and washed once with CBA. Magnetic beads containing anti-CD45 antibodies are added to the cells and allowed to react. Unreacted cells in the supernate are removed and Hoechst dye is added to the cells as a nuclear counterstain.

Flow Cytometer Use and Interpretation

The cells are then analyzed and sorted on a flow sorter based on forward and side scatter properties of the cells.

Cells which are classified as monocytic or lymphocytes are collected by flow sorting. Collected samples are deposited onto one or more slides, with no more than 10,000 cells deposited on any single slide; care is taken that deposited cells form a monolayer such that the concentration of cells on the slide is low enough so that the cells do not overlap one another.

Testing with Detection System

Slides are then tested with the detection system to detect HbF mRNA positive cells ("F+") and the presence of the X and Y chromosomes within the cells.

Example 23

Use of Anti-CD45 Antibodies Labeled with FITC and Flow Cytometry to Detect HbF mRNA and X and Y Chromosomes Preparation of Cells Twenty milliliters (20 ml) of peripheral blood from pregnant women of 10–20 weeks gestational age is collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system.

Separation of Fetal Cells from Maternal and Cord Blood

Twenty microliters (20 $\mu$l) of the cord sample is added to the 20 ml of the maternal sample. The sample is thoroughly mixed and diluted with 2 volumes of Cell Buffer A (CBA). The diluted sample is then layered on a density gradient material (e.g., Ficoll-Hypaque, Histopaque, Percoll, etc.) that has a density of 1.086 g/ml. Centrifugation and separation are carried out according to the manufacturer's instructions. The buffy-coat of cells is then collected and washed once with CBA. Anti-CD45 antibodies labeled with FITC are added to the cells and allowed to react. The cells are washed to remove unreacted antibody and Hoechst dye.

Flow Cytometer Use and Interpretation

The cells are then analyzed and sorted on a flow sorter based on (i) the fact that the cells are nucleated, (ii) the cells have forward and side scatter properties of cells which would be classified as monocytes or lymphocytes, and (iii) the cells are NEGATIVE to the CD45 antibody. Collected samples are deposited onto one or more slides, with no more than 10,000 cells deposited on any single slide; care is taken that deposited cells form a monolayer such that the concentration of cells on the slide is low enough so that cells do not overlap one another.

Testing with Detection System

Slides are then tested with the detection system to detect the HbF mRNA positive cells ("F+") and the presence of the X and Y chromosomes within the cells.

Example 24

Use of Anti-CD45 Antibodies and Flow Cytometry to Detect HbF mRNA and X and Y Chromosomes Preparation of Cells Twenty milliliters (20 ml) of peripheral blood from pregnant women of 10–20 weeks gestational age is collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system.

Separation of Fetal Cells from Maternal and Cord Blood

Twenty microliters (20 $\mu$l) of the cord sample are added to the 20 ml of the maternal sample. The sample is thoroughly mixed and diluted with 2 volumes of Cell Buffer A (CBA). The diluted sample is then layered on a density gradient material (e.g., Ficoll-Hypaque, Histopaque, Percoll, etc.) which has a density of 1.086 g/ml. Centrifugation and separation are carried out according to the manufacturer's instructions. The buffy-coat of cells is then collected and washed once with CBA. Magnetic beads containing anti-CD45 antibodies are added to the cells and allowed to react. Unreacted cells in the supernate are removed and fixed with 0.5% paraformaldehyde overnight at 4° C.

Testing with Detection System

The next day, the cells are hybridized in solution with either of the detection HbF system to detect the HbF mRNA positive cells ("F+"); when the FCI-ID system is used, the presence of the X and Y chromosomes within the cells is also detected. Following hybridization the cells are washed.

Flow Cytometer Use and Interpretation

The cells are then analyzed and sorted on a flow sorter based on (i) the fact that the cells are nucleated, (ii) the cells have forward and side scatter properties of cells which would be classified as monocytic or lymphocytes, and (iii) the cells are POSITIVE to the HbF mRNA probe. Collected samples are deposited onto one or more slides, with no more than 10,000 cells deposited on any single slide; care is taken that deposited cells formed a monolayer such that the concentration of cells on the slide is low enough so that cells did not overlap one another.

Testing with Detection System

Slides are then tested with the detection system to detect the HbF mRNA positive cells ("F+") and the presence of the X and Y chromosomes within the cells.

Example 25

Use of Anti-CD45 Antibodies Labeled with PE to Detect HbF mRNA and X and Y Chromosomes Preparation of Cells Twenty milliliters (20 ml) of peripheral blood from pregnant women of 10-20 weeks gestational age are collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system.

Separation of Fetal Cells from Maternal and Cord Blood

Twenty microliters (20 $\mu$l) of the cord sample are added to the 20 ml of the maternal sample. The sample is thoroughly mixed and diluted with 2 volumes of Cell Buffer A (CBA). The diluted sample is then layered on a density gradient material (e.g., Ficoll-Hypaque, Histopaque, Percoll, etc.) which has a density of 1.086 g/ml. Centrifugation and separation are carried out according to the manufacturer's instructions. The buffy-coat of cells is then collected and washed once with CBA. Anti-CD45 antibodies labeled with PE are added to the cells and allowed to react. The cells are washed to remove unreacted antibody and fixed with 0.5% paraformaldehyde overnight at 4° C.

Testing with Detection System

The next day, the cells are hybridized in solution with either the detection HbF or system to detect the HbF mRNA positive cells ("F+"); when the FCID-ID system is used the presence of the X and Y chromosomes within the cells is also detected. Following hybridization the cells are washed.

Flow Cytometer Use and Interpretation

The cells are then analyzed and sorted on a flow sorter based on (i) the fact that the cells are nucleated, (ii) the cells have forward and side scatter properties of cells which would be classified as monocytes or lymphocytes, (iii) the cells are POSITIVE to the HbF mRNA probe, and (iv) the cells were NEGATIVE to the CD45 antibody. Collected samples are deposited onto one or more slides, with no more than 10,000 cells deposited on any single slide; care is taken that deposited cells formed a monolayer such that the concentration of cells on the slide is low enough so that cells did not overlap one another.

Testing with Detection System

Slides are then tested with the detection system to detect the HbF mRNA positive cells ("F+") and the presence of the X and Y chromosomes within the cells.

Example 26

Use of Anti-CD45 Antibodies Labeled with PE to Detect HbF mRNA and X and Y Chromosomes Preparation of Cells Twenty milliliters (20 ml) of peripheral blood from pregnant women of 10–20 weeks gestational age are collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system.

Separation of Fetal Cells from Maternal and Cord Blood

Twenty microliters (20 $\mu$l) of the cord sample are added to the 20 ml of the maternal sample. The sample is thoroughly mixed and diluted with 2 volumes of Cell Buffer A (CBA). The diluted sample is then layered on a density gradient material (e.g., Ficoll-Hypaque, Histopaque, Percoll, etc.) which has a density of 1.086 g/ml. Centrifugation and separation are carried out according to the manufacturer's instructions. The buffy-coat of cells is then collected and washed once with CBA. Anti-CD45 antibodies labeled with PE are added to the cells and allowed to react. The cells are washed to remove unreacted antibody and fixed with 0.5% paraformaldehyde overnight at 4° C.

Testing with Detection System

The next day, the cells are hybridized in solution with either the detection HbF/HbA or system to detect the HbF mRNA positive cells ("F+") and the HbA positive cells ("A+"); when the FCI-ID system is used the presence of the X and Y chromosomes within the cells are also detected. Following hybridization the cells are washed.

Flow Cytometer Use and Interpretation

The cells are then analyzed and sorted on a flow sorter based on (i) the fact that the cells are nucleated, (ii) the cells have forward and side scatter properties of cells which would be classified as monocytic or lymphocytes, (iii) the cells are POSITIVE to the HbF mRNA probe, (iv) the cells are NEGATIVE to the HbA mRNA probe, and (v) the cells are NEGATIVE to the CD45 antibody. Collected samples are deposited onto one or more slides, with no more than 10,000 cells deposited on any single slide; care is taken that deposited cells formed a monolayer such that the concentration of cells on the slide is low enough so that cells did not overlap one another.

Testing with Detection System

Slides are then tested with the detection system to detect the HbF mRNA positive cells ("F+") and the presence of the X and Y chromosomes with the cells.

Example 27

Use of Anti-CD45 Antibodies Labeled with PE (or FITC) to Detect HbF mRNA and X and Y Chromosomes Preparation of Cells Twenty milliliters (20 ml) of peripheral blood from pregnant women of 10–20 weeks gestational age are collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 $\mu$l of cord blood and the detection HbF system.

Separation of Fetal Cells from Maternal and Cord Blood

Twenty microliters (20 $\mu$l) of the cord sample are added to the 20 ml of the maternal sample. The sample is thoroughly mixed and diluted with 2 volumes of Cell Buffer A (CBA). The diluted sample is then layered on a density gradient material (e.g., Ficoll-Hypaque, Percoll, etc.) which has a density of 1.086 g/ml. Centrifugation and separation are carried out according to the manufacturer's instructions. The buffy-coat of cells is then collected and washed once with CBA. Anti-CD45 antibodies labeled with PE (or FITC) are added to the cells and allowed to react. The cells are washed to remove unreacted antibody and fixed with 0.5% paraformaldehyde overnight.

Testing with Detection HbA-System

The next day, the cells are hybridized in solution with the detection HbA system to detect the HbA positive cells ("A+"). Following hybridization the cells are washed.

Flow Cytometer Use and Interpretation

The cells are then analyzed and sorted on a flow sorter based on (i) the fact that the cells are nucleated, (ii) the cells have forward and side scatter properties of cells which would be classified as monocytic or lymphocytes, (iii) the cells are NEGATIVE to the HbA mRNA probe, and (iv) the cells are NEGATIVE to the CD45 antibody. Collected samples are deposited onto one or more slides, with no more than 10,000 cells deposited on any single slide; care is taken that deposited cells form a monolayer such that the concentration of cells on the slide is low enough so that cells do not overlap one another.

Testing with Detection System

Slides are then tested with the detection system to detect the HbF mRNA positive cells ("F+") and the presence of the X and Y chromosomes within the cells.

Example 28

Use of Anti-CD45 Antibodies Labeled with FITC and Flow Cytometry to Detect Trophoblast mRNA and X and Y Chromosomes Preparation of Cells Twenty milliliters (20 ml) of peripheral blood from a pregnant women of 10–20 weeks gestational age are collected in blood collection tubes containing EDTA. Separately, 1–5 ml of an umbilical cord blood sample from the birth of a male child is collected in blood collection tubes containing EDTA. Both the maternal blood sample ("maternal") and the umbilical cord blood ("cord") blood sample are typed. Only samples which have the same type are used. The total number of nucleated red blood cells ("nRBC") and the number of nucleated red blood cells which contain the fetal hemoglobin mRNA ("F+") are determined using 20 μl of cord blood and the detection HbF system.

Separation of Fetal Cells from Maternal and Cord Blood

Twenty microliter (20 μl) of the cord sample are added to the 20 ml of the maternal sample. The sample is thoroughly mixed and diluted with 2 volumes of Cell Buffer A (CBA). The diluted sample is then layered on a density gradient material (e.g., Ficoll-Hypaque, Percoll, etc.) which has a density of 1.086 gm/ml. Centrifugation and separation are carried out according to the manufacturer's instructions. The buffy-coat of cells is then collected and washed once with CBA. Anti-CD45 antibodies labeled with FITC are added to the cells and allowed to react. The cells are washed to remove unreacted antibody and Hoechst is added to the cells as a nuclear counter-stain.

Flow Cytometer Use and Interpretation

The cells are then analyzed and sorted on a flow sorter based on (i) the fact that the cells are nucleated, (ii) the cells have forward and side scatter properties of cells which would be classified as multi-nucleated or trophoblasts, and (iii) the cells are NEGATIVE to the CD45 antibody. Collected samples are deposited onto one or more slides, with no more than 10,000 cells deposited on any single slide; care is taken that deposited cells form a monolayer such that the concentration of cells on the slide is low enough so that cells do not overlap one another.

Testing with Detection System

Slides are then tested with the detection system to detect the trophoblast-specific mRNA positive cells ("TR+") and the presence of the X and Y chromosomes within the cells.

Example 29

Identification of fetal cells by light scatter properties

Preparation of Cells

Twenty milliliters (20 ml) of peripheral blood from a male donor was collected in Vacutainer tubes containing EDTA.

Separation of Fetal Cells from an Adult Donor Blood

The sample was thoroughly mixed and diluted with 2 volumes of Cell Buffer A (CBA). The diluted sample was then layered on a density gradient material (e.g., Ficoll-Hypaque, Percoll, etc.) which has a density of 1.086 gm/ml. Centrifugation and separation are carried out according to the manufacturer's instructions. The buffy-coat of cells is then collected and washed once with CBA. A portion of the buffy-coat was then mixed with anti-CD45 antibodies labeled with PE (or FITC) are added to the cells and allowed to react.

Flow Cytometer Use and Interpretation

The cells treated with anti-CD45 were sorted to select cells that are positive with respect to staining by the anti-body. The cells are then analyzed and sorted on a flow sorter based on the fact that the cells have forward and side scatter properties of cells which would be classified as having monocytic, lymphocytic or granulocytic properties. The proportion of cells in each light-scattering class staining positive with the anti-CD45 antibody was determined and the results are presented in the table below. Collected samples are deposited onto one or more slides, with no more than 10,000 cells deposited on any single slide; care is taken that deposited cells form a monolayer such that the concentration of cells on the slide is low enough so that cells do not overlap one another.

TABLE 14

| Sample Number | Lymphocytes | Monocytes | Granulocytes |
|---|---|---|---|
| A | 99.5 | 92.7 | 88.2 |
| B | 94.2 | 99.9 | 98.8 |
| C | 90.9 | 99.4 | 97.6 |
| D | 99.9 | 99.9 | 99.5 |
| E | 84.2 | 96.3 | 73.9 |
| F | 99.5 | 99.8 | 99 |
| G | 99.8 | 100 | 97.4 |
| H | 97.4 | 99.4 | 99.2 |
| I | 99.9 | 100 | 91.8 |
| J | 90.6 | 98.8 | 97.8 |
| Mean | 95.6 | 98.6 | 94.3 |

Example 30

Identification of leukocyte cell class by CD45 binding scatter properties

Preparation of Cells

Twenty milliliters (20 ml) of peripheral blood from a male donor was collected in Vacutainer tubes containing EDTA. Separately, 1–5 ml of an umbilical cord blood sample from the birth of a female child was collected in Vacutainer tubes containing EDTA. Both the male blood sample and the umbilical cord blood ("cord") blood sample were typed. Only samples which had the same blood-type were used.

Separation of Fetal Cells from Adult Donor Blood

A portion of the cord sample (1.5 ml) was added to 15 ml of the adult sample. The sample was thoroughly mixed and diluted with 2 volumes of Cell Buffer A (CBA). The diluted sample was then layered on a density gradient material (e.g., Ficoll-Hypaque, Percoll, etc.) which has a density of 1.086 gm/ml. Centrifugation and separation are carried out according to the manufacturer's instructions. The buffy-coat of cells is then collected and washed once with CBA. A portion of the buffy-coat was then mixed with anti-CD45 antibodies labeled with PE (or FITC) and allowed to react. Another portion of the buffy-coat cells was subjected to flow sorting without anti-CD45 treatment. A final portion of the buffy-coat cells were reacted with magnetic beads coated with anti-CD45 antibodies which were then removed with reacted cells attached prior to flow sorting.

Flow Cytometer Use and Interpretation

The cells were then analyzed and sorted on a flow sorter based on the fact that the cells have forward and side scatter properties of cells which would be classified as mono-nuclear. The cells treated with anti-CD45 were also sorted to select cells that are negative with respect to staining by the anti-CD45 antibody. Collected samples are deposited onto one or more slides, with no more than 10,000 cells deposited on any single slide; care is taken that deposited cells form a monolayer such that the concentration of cells on the slide is low enough so that cells do not overlap one another.

Testing with Detection System

Slides were then tested with the detection system to detect presence of the X and Y chromosomes within the cells and the results are shown in the Table below.

TABLE 15

| Cell Treatment | Cell Number | Female cells | Male cells | Female (%) |
|---|---|---|---|---|
| Density gradient | $4.1 \times 10^5$ | 50 | 51 | 49.5 |
| Density gradient + Sorting on scatter | $2.7 \times 10^4$ | 41 | 68 | 37.6 |
| Density gradient + Depletion of CD45+ + Sorting on scatter | $0.2 \times 10^4$ | 32 | 0 | 100 |
| Density gradient + Sorting on CD45 + Sorting on scatter | $0.1 \times 10^4$ | 19 | 2 | 90.4 |

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Having thus described the invention, what is claimed is:

1. A method for distinguishing individual fetal cells from adult cells in a blood specimen, said method comprising:
   (i) processing a blood specimen from a pregnant female to yield a mixture of cells, said mixture of cells comprising fetal cells and adult cells;
   (ii) treating said mixture of cells with a fixing agent to form a mixture of permeabilized fixed cells;
   (iii) reacting said mixture of fixed cells with a detectably-labeled antibody specific for an antigen selectively produced by target fetal cells, said antigen being selected from the group consisting of:
      embryonic hemoglobin, fetal hemoglobin, cytokeratin, β-subunit of chorionic gonadotropin, chorionic somatomammotropin and pregnancy-specific glycoprotein;
   (iv) separating said cells from unreacted antibodies; and
   (v) detecting said detectably-labeled antibody remaining within said cells; whereby detection of said detectably-labeled antibody permits identification of such cells as fetal cells.

2. The method of claim 1, wherein:
   said detectably-labeled antibody is labeled with a fluorescer selected from the group consisting of fluorescein, coumarin, rhodamine, rhodamine derivatives, cyanine dyes and phycoerythrin, and
   said step (v) of detecting said detectably-labeled antibody is achieved by use of an instrument selected from the group consisting of a fluorescence microscope and a flow cytometer.

3. The method of claim 2, additionally comprising:
   depositing said mixture of cells on a solid support before performing said steps (ii) through (iv), and said step (v) of detecting said detectably-labeled antibody is performed by use of a fluorescence microscope.

4. The method of claim 2, wherein step (v) of detecting said detectably-labeled antibody comprises:
   passing said mixture of cells through a flow cytometer; and
   detecting a fluorescent signal emitted by individual cells passing through the excitatory beam of said flow cytometer.

5. The method of claim 1, wherein step (i) of processing a blood specimen comprises the steps:
   (a) treating said blood specimen to prevent coagulation, thereby obtaining an uncoagulated blood specimen;
   (b) placing into a centrifuge tube at least one layer of density gradient material;
   (c) overlayering said layer of density gradient material with a layer of said uncoagulated blood specimen;
   (d) subjecting said centrifuge tube to a force field in a manner whereby erythrocytes pass below a layer of density gradient material and nucleated cells are preferentially retained at an interface of density gradient material; and
   (e) recovering said nucleated cells from said interface; whereby said nucleated cells are used as said cells of step (iii) of claim 1.

6. The method of claim 1, wherein said blood specimen is collected from a pregnant woman and step (i) of processing a blood specimen comprises the steps:
   (a) treating said blood specimen to prevent coagulation, thereby obtaining an uncoagulated blood specimen;
   (b) contacting said uncoagulated blood specimen with antibodies to an antigen that is present on adult cells but not on said target fetal cells, thereby forming antibody-bound cells;
   (c) removing said antibody-bound cells from said uncoagulated blood specimen, and
   (d) recovering cells remaining in said uncoagulated blood specimen. whereby said nucleated cells are used as said cells of step (iii) of claim 1.

7. A method for determining the presence of a target nucleotide sequence in individual fetal cells present in a cellular specimen, said method comprising:
   (i) processing a cellular specimen to yield a mixture of cells, said mixture of cells comprising fetal cells and adult cells;
   (ii) treating said mixture of cells with a fixing agent to form a mixture of permeabilized fixed cells;
   (iii) reacting said mixture of fixed cells with a detectably-labeled antibody specific for an antigen selectively produced by fetal cells, said detectably-labeled antibody bearing a first detectable label, and said antigen being selected from the group consisting of:
      embryonic hemoglobin, fetal hemoglobin, cytokeratin, β-subunit of chorionic gonadotropin, chorionic somatomammotropin and pregnancy-specific glycoprotein;
   (iv) separating said fixed cells from unreacted antibodies;
   (v) performing in situ hybridization on said fixed cells under hybridizing conditions suitable to maintain cell membranes in a substantially intact state and with a hybridization medium comprising a detectably-labeled probe complementary to a target nucleotide sequence, said detectably-labeled probe bearing a second detectable label distinguishable from said first detectable label;
   (vi) removing said hybridization medium together with unhybridized probe from said fixed cells; and
   (vii) detecting a first signal of said first label and a second signal of said second label remaining in said fixed cells; whereby cells in which said first and said second signal are detected are characterized as being fetal cells in which said target nucleotide sequence is present.

8. The method of claim 7, wherein:

said hybridization medium comprises a denaturing agent, a hybrid stabilizing agent, a buffering agent, and a membrane pore-forming agent; and said hybridizing conditions comprise incubation at a temperature in the range 37° C. to 85° C. for a time from 5 minutes to 2 hours.

9. The method of claim 7, wherein said step (vii) is performed with an instrument selected from the group consisting of a fluorescence microscope and a flow cytometer.

10. The method of claim 7, wherein said target nucleotide sequence is a nucleotide sequence characteristic of a chromosome selected from the group consisting of: human chromosome X, human chromosome Y, human chromosome 1, human chromosome 13, human chromosome 16, human chromosome 18, and human chromosome 21;

said method further comprising:
(a) determining the quantity of said second signal emitted by said second label within said individual fetal cells;
(b) determining a normal quantity of second signal, said normal quantity of second signal being emitted by said second detectable label within individual cells known to have a normal karyotype;
(c) comparing said quantity of said second signal in individual fetal cells with said normal quantity of second signal emitted from cells known to a normal karyotype; wherein
determination of a subnormal quantity of said signal emitted from said probe label within said individual fetal cells is indicative of a genetic deletion in said individual fetal cells;
determination of a normal quantity of said signal emitted from said probe label within said individual fetal cells is indicative of a normal genetic status in said individual fetal cells; and
determination of a supranormal quantity of said signal emitted from said probe label within said individual fetal cells is indicative of a genetic duplication or amplification in said individual fetal cells.

11. The method of claim 7, wherein:

said target nucleotide sequence is a nucleotide sequence characteristic of a virus selected from the group consisting of human immunodeficiency virus, hepatitis virus and herpes virus; and said method further comprises:
(a) determining a quantity of said second signal emitted by said second label within said individual fetal cells;
(b) determining a quantity of said second signal emitted by said second label within individual cells known to be not virally infected;
(c) comparing said quantity of second signal emitted by individual fetal cells with said quantity of said second signal emitted by individual cells known not to be virally infected; wherein
determination of a normal quantity of signal emitted by said second label within said individual fetal cells is indicative of the absence of said target virus nucleic acid in said individual fetal cells; and
determination of a supranormal quantity of signal emitted by said second label within said individual fetal cells is indicative of the presence of said target virus nucleic acid in said individual fetal cells.

12. The method of claim 7, wherein:

said target nucleotide sequence is a messenger ribonucleic acid selected from the group consisting of: human immunodeficiency virus messenger ribonucleic acid, hepatitis virus messenger ribonucleic acid, and herpes virus messenger ribonucleic acid; and said method further comprises:
(a) determining a quantity of said second signal emitted by said second label within said individual fetal cells;
(b) determining a quantity of said second signal emitted by said second label within individual cells known to be not virally infected;
(c) comparing said quantity of second signal emitted by individual fetal cells with said quantity of said second signal emitted by individual cells known not to be virally infected;

wherein determination of a supranormal quantity of signal emitted by said second label within said individual fetal cells is indicative of the presence of said target virus messenger ribonucleic acid in said individual fetal cells.

13. The method of claim 7, additionally comprising:
(a) passing said suspension of cells through a flow cytometer;
(b) detecting with said flow cytometer said signal emitted by said first label;
(c) detecting with said flow cytometer said signal emitted by said second label;
(d) characterizing cells wherein said first signal is emitted as fetal cells; and characterizing cells wherein said first and said second signal are emitted, as virally infected fetal cells.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

ATCGAGTAGT GGTATTTCAC CGGC        24

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TACGCTCGAT CCAGCTATCA GCCGT        25

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CGGCGGCGGC GGCGGCGGCG GCGGC                                              25

( 2 ) INFORMATION FOR SEQ ID NO:4:

( i ) SEQUENCE CHARACTERISTICS:
        ( A ) LENGTH: 443 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( x i ) SEQUENCE DESCRIPTION: SEQ ID NO:4:

ATGGGTCATT TCACAGAGGA GGACAAGGCT ACTATCACAA GCCTGTGGGG     50

CAAGGTGAAT GTGGAAGATG CTGGAGGAGA AACCCTGGGA AGCTCCTGGT    100

TGTCTACCCA TGGACCCAGA GGTTCTTTGA CAGCTTTGGC AACCTGTCCT    150

CTGCCTCTGC CATCATGGGC AACCCCAAAG TCAAGGCACA TGGCAAGAAG    200

GTGCTGACTT CCTTGGGAGA TGCCATAAAG CACCTGGATG ATCTCAAGGG    250

CACCTTTGCC CAGCTGAGTG AACTGCACTG TGACAAGCTG CATGTGGATC    300

CTGAGAACTT CAAGCTCCTG GGAAATGTGC TGGTGACCGT TTTGGCAATC    350

CATTTCGGCA AAGAATTCAC CCCTGAGGTG CAGGCTTCCT GGCAGAAGAT    400

GGTGACTGGA GTGGCCAGTG CCCTGTCCTC CAGATACCAC TGA           443

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:5:

TCAGTGGTAT CTGGAGGACA GGGCA                                              25

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:6:

CTGGCCACTC CAGTCACCAT CTTCT                                              25

( 2 ) INFORMATION FOR SEQ ID NO:7:

( i ) SEQUENCE CHARACTERISTICS:

( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:7:

GCCAGGAAGC CTGCACCTCA GGGGT                                                                25

( 2 ) INFORMATION FOR SEQ ID NO:8:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:8:

GAATTCTTTG CCGAAATGGA TTGCC                                                                25

( 2 ) INFORMATION FOR SEQ ID NO:9:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:9:

AAAACGGTCA CCAGCACATT TCCCA                                                                25

( 2 ) INFORMATION FOR SEQ ID NO:10:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:10:

GGAGCTTGAA GTTCTCAGGA TCCAC                                                                25

( 2 ) INFORMATION FOR SEQ ID NO:11:

( i ) SEQUENCE CHARACTERISTICS:
                    ( A ) LENGTH: 25 base pairs
                    ( B ) TYPE: nucleic acid
                    ( C ) STRANDEDNESS: single
                    ( D ) TOPOLOGY: linear ( i i ) MOLECULE TYPE: cDNA to mRNA ( i i i ) HYPOTHETICAL:

( x i ) SEQUENCE DESCRIPTION: SEQ ID NO:11:

ATGCAGCTTG TCACAGTGCA GTTCA                                                                25

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:12:

CTCAGCTGGG CAAAGGTGCC CTTGA     25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:13:

GATCATCCAG GTGCTTTATG GCATC     25

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:14:

TCCCAAGGAA GTCAGCACCT TCTTG     25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:15:

CCATGTGCCT TGACTTTGGG GTTGC     25

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:16:

CCATGATGGC AGAGGCAGAG GACAG 25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:17:

GTTGCCAAAG CTGTCAAAGA ACCTC 25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:18:

TGGGTCCATG GGTAGACAAC CAGGA 25

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL:

( x i ) SEQUENCE DESCRIPTION: SEQ ID NO:19:

GCTTCCCAGG GTTTCTCCTC CAGCA 25

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:20:

TCTTCCACAT TCACCTTGCC CCACA 25

( 2 ) INFORMATION FOR SEQ ID NO:21:

( i ) SEQUENCE CHARACTERISTICS:
        ( A ) LENGTH: 25 base pairs
        ( B ) TYPE: nucleic acid

```
        ( C ) STRANDEDNESS: single
        ( D ) TOPOLOGY: linear ( i i ) MOLECULE TYPE: cDNA to mRNA ( i i i ) HYPOTHETICAL: N ( x i ) SEQUENCE DESCRIPTION: SEQ ID NO:21:

GGCTTGTGAT    AGTAGCCTTG    TCCTC                                         2 5
```